United States Patent
Karasawa et al.

(10) Patent No.: US 10,571,250 B2
(45) Date of Patent: Feb. 25, 2020

(54) MEASURING DEVICE, SYSTEM, METHOD, AND PROGRAM

(71) Applicant: 3M INNOVATIVE PROPERTIES COMPANY, St. Paul, MN (US)

(72) Inventors: Fumio Karasawa, Tokyo (JP); Andreas M. Geldmacher, Dormagen (DE); Guruprasad Somasundaram, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 228 days.

(21) Appl. No.: 15/735,868

(22) PCT Filed: Jun. 28, 2016

(86) PCT No.: PCT/US2016/039756
§ 371 (c)(1),
(2) Date: Dec. 12, 2017

(87) PCT Pub. No.: WO2017/004008
PCT Pub. Date: Jan. 5, 2017

(65) Prior Publication Data
US 2019/0339063 A1 Nov. 7, 2019

Related U.S. Application Data

(60) Provisional application No. 62/187,322, filed on Jul. 1, 2015.

(51) Int. Cl.
*G01B 11/14* (2006.01)
*G01B 11/30* (2006.01)
(Continued)

(52) U.S. Cl.
CPC ............. *G01B 11/14* (2013.01); *G01B 11/30* (2013.01); *G01N 21/251* (2013.01);
(Continued)

(58) Field of Classification Search
CPC ........... G01B 11/14; G01B 11/30; G06T 7/80; H04N 13/246; G01N 21/251; G01N 21/274; G01N 2021/551
See application file for complete search history.

(56) References Cited

U.S. PATENT DOCUMENTS

| 5,410,407 A | 4/1995 | Zielinski et al. |
| 6,166,813 A | 12/2000 | Roberts |

(Continued)

FOREIGN PATENT DOCUMENTS

| EP | 1586919 | 6/2017 |
| JP | 61-243346 | 10/1986 |

(Continued)

OTHER PUBLICATIONS

International Search Report PCT/US16/39756, dated Sep. 26, 2016, 2 pages.

*Primary Examiner* — Jamil Ahmed
(74) *Attorney, Agent, or Firm* — Christopher D. Karlen

(57) ABSTRACT

Problem: To provide a device, system, method, and program able to easily measure retroreflective coefficients using a commercially available mobile terminal having an imaging unit. Resolution Means: A device is provided that has an imaging unit for capturing an image of a target object, an observation angle acquiring unit for acquiring an observation angle determined by a positional relationship between the imaging unit, a light source for emitting light for capture and the target object, an entrance angle acquiring unit for acquiring an entrance angle of light emitted for capture incident on the target object, a converting unit for converting image data of an image to a luminance value of the target object using capture information of the image, and a calculating unit for calculating a value of a retroreflective coefficient of the target object based on an illuminance value and the luminance value of the target object.

16 Claims, 13 Drawing Sheets

(51) Int. Cl.
*G01N 21/27* (2006.01)
*H04N 13/246* (2018.01)
*G01N 21/25* (2006.01)
*G06T 7/80* (2017.01)
*G01N 21/55* (2014.01)

(52) U.S. Cl.
CPC ............ *G01N 21/274* (2013.01); *G06T 7/80* (2017.01); *H04N 13/246* (2018.05); *G01N 2021/551* (2013.01)

(56) References Cited

U.S. PATENT DOCUMENTS

| | | | |
|---|---|---|---|
| 7,961,328 B2 | 6/2011 | Austin et al. | |
| 8,262,238 B1 | 9/2012 | Chapman | |
| 2010/0131235 A1 | 5/2010 | Aoba | |
| 2012/0128940 A1 | 5/2012 | Kamiyama | |
| 2013/0194565 A1 | 8/2013 | Sorensen et al. | |
| 2013/0271613 A1 | 10/2013 | Retterath et al. | |
| 2014/0313504 A1* | 10/2014 | Gutierrez Mendez | G01N 21/55 356/72 |
| 2016/0321823 A1 | 11/2016 | Karasawa | |
| 2016/0321824 A1 | 11/2016 | Karasawa | |
| 2016/0321825 A1 | 11/2016 | Karasawa et al. | |

FOREIGN PATENT DOCUMENTS

| | | |
|---|---|---|
| JP | 2001-091222 | 4/2001 |
| JP | 2001-324410 | 11/2001 |
| JP | 2002-206989 | 7/2002 |
| JP | 2009-000441 | 10/2009 |
| WO | WO 2005-063068 | 7/2005 |
| WO | WO 2006-091968 | 8/2006 |
| WO | WO 2011154617 | 12/2011 |

* cited by examiner

| Observation Angle φ | Entrance Angle θ |
|---|---|
| 12'± $\Delta\phi$ | 5°± $\Delta\theta$ |
| 20'± $\Delta\phi$ | 20°± $\Delta\theta$ |
| 1°± $\Delta\phi$ | 30°± $\Delta\theta$ |
| 1°30'± $\Delta\phi$ | 40°± $\Delta\theta$ |
| : | : |

*Fig. 6A*

| Illuminance Value I(1x) | Observation Angle φ | Entrance Angle θ | Light Source Type |
|---|---|---|---|
| I1 | 12' | 5° | |
| I2 | 20' | 20° | |
| I3 | 1° | 30° | |
| I4 | 1°30' | 40° | |
| : | : | : | : |

*Fig. 6B*

MEASURING DEVICE, SYSTEM, METHOD, AND PROGRAM

CROSS REFERENCE TO RELATED APPLICATIONS

This application is a national stage filing under 35 U.S.C. 371 of PCT/US2016/039756, filed Jun. 28, 2016, which claims the benefit of Provisional Application No. 62/187,322, filed Jul. 1, 2015, the disclosure of which is incorporated by reference in its/their entirety herein.

TECHNICAL FIELD

The present invention relates to a measuring device, system, method, and program.

BACKGROUND

FIG. 13 is a drawing for describing a retroreflective material. Retroreflection is defined as a phenomenon where incident light is reflected back in the direction of incidence regardless of entrance angle. A retroreflective material 80 is configuration of a coating 82 of clear synthetic resin containing a multiplicity of fine particles (beads) 81. Incident light 83 incident on the retroreflective material 80 is refracted inside the particles 81, and then reflected after being focused to one point to become reflected light 84 that once more passes through the particles 81 and returns back in an original direction. Therefore, when viewed from the incident direction of the light, a retroreflective material appears to glow, but does not appear to glow when viewed from a direction different than the incident direction of the light. Furthermore, the retroreflective material 80 can be realized using a different configuration such as a prism formed into a three dimensional shape and the like.

While retroreflective material is widely used in, for example, guide signs, clothing (garment), and the like, the properties thereof must be examined to determine product lifetime since retroreflective performance diminishes with use. One characteristic of retroreflective material is a retroreflective coefficient ($cd/m^2 lx$) defined by the ratio of a retroreflective luminance ($cd/m^2$) relative to an incident light illuminance (lx). The value of the retroreflective coefficient is used not only in quantifying properties but can also be used as an index for determining product lifetime for retroreflective material. For example, devices and methods for measuring the retroreflective performance of retroreflective material used in road signs, clothing, and the like are described in Patent Documents 1 and 2.

DOCUMENTS OF THE RELATED ART

Patent Documents

Patent Document 1: US Patent Application Publication No. 2013/0194565
Patent Document 2: U.S. Pat. No. 7,961,328

SUMMARY OF THE INVENTION

Problem to be Solved by the Invention

Methods for measuring retroreflective coefficients are defined by industrial standards such as ANSI 107-2010, JIS Z8714-1995, and the like. These standards not only define photometric values for luminance and illuminance and the like, but also define geometric conditions at the measurement of such things as the entrance angle of irradiating light incident on a retroreflective material and the observation angle between a light source and a detector. To measure retroreflective coefficients that satisfy such measurement conditions, large scale and expensive instruments, like, for example, those described in Patent Documents 1 and 2, are required.

Thus, an object of the present invention is to provide a device, system, method, and program able to easily measure retroreflective coefficients using a commercially available mobile terminal having an imaging unit.

Means for Solving the Problem

A device is provided that has an imaging unit for capturing an image of a target object, an observation angle acquiring unit for acquiring an observation angle determined by a positional relationship between the imaging unit, a light source for emitting light for capture and the target object, an entrance angle acquiring unit for acquiring an entrance angle of light emitted for capture incident on the target object, a converting unit for converting image data of an image to a luminance value of the target object using capture information of the image, and a calculating unit for calculating a value of a retroreflective coefficient of the target object based on an illuminance value and the luminance value of the target object.

It is preferable that the device described above also have an output unit for outputting the values of the observation angle, the entrance angle, and the retroreflective coefficient.

It is preferable that the device described above also have a light emitting unit that is the light source for emitting light for capture.

It is preferable that the device described above also have a determining unit that determines whether the observation angle and the entrance angle are included within a range of reference, and that the output unit also output determination results according to the determining unit.

It is preferable that the device described above also have a storage unit for storing a correspondence relationship between the observation angle and the entrance angle that determines the range of reference.

In the device described above, it is preferable that the storage unit record a plurality of correspondence relationships based on the type of the target object, and that the determining unit reference correspondence relationships according to the type of the target object to be captured, and then determine whether the observation angle and the entrance angle are included within the obtained range of reference.

In the device described above, it is preferable that the storage unit also record a second correspondence relationship between the type of the light source, the observation angle, the entrance angle, and the illuminance value of the target object.

In the device described above, it is preferable that the imaging unit, in addition to capturing a first image of the target object using the light emitted for capture, also capture a second image of the target object without using the light emitted for capture, and that the conversion unit, in addition to converting the image data of the first image to a first luminance value, also convert the image data of the second image to a second luminance value, and then acquire a luminance value of the target object by calculating the difference between the first luminance value and the second luminance value.

In the device described above, it is preferable that the imaging unit capture images that include portions other than the target object, and that the conversion unit correct the luminance value of the target object based on the portions other than the target object obtained from the image data of the image.

It is preferable that the device described above also have an illuminance value calculating unit for calculating an illuminance value of the target object based on a luminance value of a retroreflective material when light is irradiated from the light source onto a retroreflective material for which a retroreflective coefficient is known.

In the device described above, it is preferable that the imaging unit, regardless of the operation of a user, capture an image of the target object when it has been determined that the observation angle and the entrance angle are included within the range of reference.

In the device described above, it is preferable that the output unit be a display unit for displaying an area captured by the imaging unit, determination results of the determining unit, and the value of the retroreflective coefficient calculated by the calculating unit.

It is preferable that the device described above also have an exposure correcting unit for adjusting an exposure amount during capture by the imaging unit.

It is preferable that the device described above also have a filter for reducing the intensity of light from the light source.

It is preferable that the device described above also have a prism for deflecting the light path of the light from the light source to adjust the observation angle.

It is preferable that the device described above also have a reference target object that includes one or a plurality of retroreflective areas for which the retroreflective coefficients are known, and that the calculating unit perform calculation using the feature values of the one or the plurality of retroreflective areas.

In the device described above, it is preferable that the reference target object include a plurality of retroreflective areas for which the values of the retroreflective coefficients are known, and that the retroreflective coefficients of the plurality of retroreflective areas all be different from one another.

In the device described above, it is preferable that the plurality of retroreflective areas be arranged on the reference target object in a pattern determined in advance.

A system is provided that is a system including a terminal device and a server device that are capable of communicating, where the terminal device has; an imaging unit for capturing an image of a target object; an observation angle acquiring unit for acquiring an observation angle determined by a positional relationship between the imaging unit, a light source for emitting light for capture, and the target object; an entrance angle acquiring unit for acquiring an entrance angle of light emitted for capture incident on the target object; a terminal communication unit for sending image data of an image to the server device and receiving a value of a retroreflective coefficient for the target object from the server device; and a display unit for displaying the values of the observation angle, the entrance angle, and the retroreflective coefficient, and where the server device has; a conversion unit for converting image data to a luminance value of the target object using capture information of the image data; a calculating unit for calculating a retroreflective coefficient for the target object based on an illuminance value and a luminance value of the target object; and a server communication unit for receiving image data from the terminal device and sending the value of the retroreflective coefficient to the terminal device.

Furthermore, a method is provided that has; a step for acquiring an observation angle determined by a positional relationship between an imaging unit for capturing an image of a target object, a light source for emitting light for capture, and the target object; a step for acquiring an entrance angle of light emitted for capture incident on the target subject; a step for irradiating light from the light source onto the target object; a step for capturing an image of the target object; a step for converting image data of an image to a luminance value of the target object using capture information of the image; and a step for calculating a value of a retroreflective coefficient for the target object based on an illuminance value and a luminance value of the target subject.

Furthermore, a program that; acquires an observation angle determined by a positional relationship between an imaging unit for capturing an image of a target object, a light source for emitting light for capture, and the target object; acquires an entrance angle of light emitted for capture incident on the target subject; converts image data of an image to a luminance value of the target object using capture information of an image of the target object captured by the imaging unit; and calculates a value of a retroreflective coefficient for the target object based on an illuminance value and a luminance value of the target subject, is provided in a computer.

Effect of the Invention

According to the device, system, method, and program described above, retroreflective coefficients can easily be measured using a commercially available mobile terminal having an imaging unit.

BRIEF DESCRIPTION OF THE DRAWINGS

FIG. 6A is a table showing examples of observation angles $\varphi$ and entrance angles $\theta$ that determine a range of reference.

FIG. 6B is a table showing correspondence relationships between types of light sources, the observation angles $\varphi$, the entrance angles $\theta$, and illuminance values I of a target object.

DESCRIPTION OF THE PREFERRED EMBODIMENTS

A measuring device, system, method, and program will be described in detail below with reference to the attached drawings. However, the technical scope of the present invention is not intended to be limited to the embodiments, and it should be noted that the present invention extends to the inventions according to the scope of patent claims and to equivalents thereof.

Figure 1:
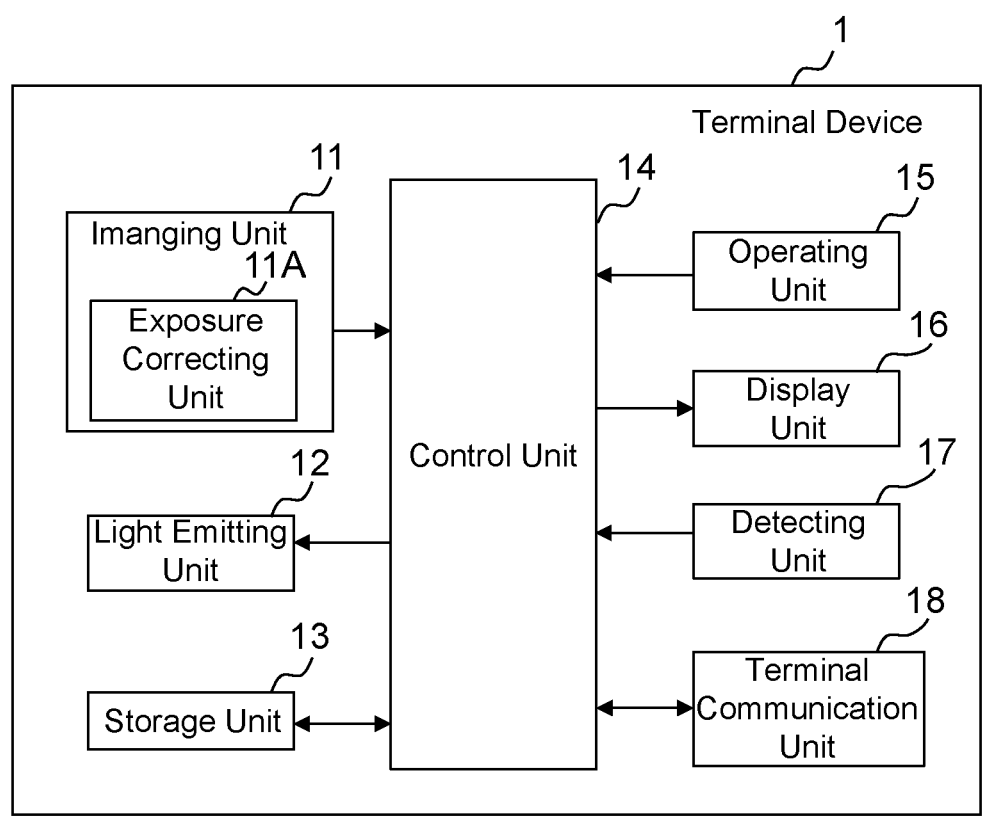
FIG. 1 is a schematic configuration diagram of a terminal device 1.

FIG. 1 is a schematic configuration diagram of a terminal device 1. The terminal device 1 has an imaging unit 11, a light emitting unit 12, a storage unit 13, a control unit 14, an operating unit 15, a display unit 16, a detecting unit 17, and a terminal communication unit 18. Terminal device 1 acquires an entrance angle and an observation angle that show a positional relationship between the terminal device itself and a target to be measured using an internally mounted sensor. The terminal device 1 is, for example, a mobile terminal such as a smart phone or the like equipped with an internally mounted camera.

The imaging unit 11 corresponds to a camera internally mounted in the terminal device 1, captures an image of a target object using a format such as RAW (DNG) data, JPEG (JFIF) data, sRGB data, or the like, and acquires image data for a target to be measured. While any of these data formats are acceptable, most of the examples described below are of cases where the imaging unit 11 acquires JPEG (JFIF) data. For example, based on an operation by a user, the imaging unit 11 captures a first image of the target object using light emitted for capture and, at the same time, also captures a second image of the target object without using the light emitted for capture.

An exposure correcting unit 11A adjusts an exposure amount during capture by the imaging unit 11 to correspond to at least one of an aperture, a shutter speed adjusting unit, or an ISO sensitivity adjusting unit of a camera of the imaging unit 11. For example, if a luminance value calculated from a captured image is too high, the exposure correcting unit 11A is used to adjust the luminance value to a value within a suitable range. Exposure amount correction using the exposure correcting unit 11A can be done either manually by a user or automatically by the imaging unit 11.

The light emitting unit 12 is an LED (a torch or a flash) that is a light source for emitting light for capture that emits light as needed during capture by the imaging unit 11. The light emitting unit 12 is preferably placed next to a lens of the imaging unit 11. By doing this, a direction from which light emitted for capture incidents on and is reflected from a retroreflective material and a direction in which the imaging unit 11 captures become nearly the same direction, and thus a large amount of reflected light due to retroreflection can be captured.

The storage unit 13 is, for example, semiconductor memory that stores image data captured by the imaging unit 11, data required for the operation of the terminal device 1, and the like. The control unit 14 is configured of a CPU, RAM, ROM, and the like, and controls the operation of the terminal device 1. The operating unit 15 is configured of, for example, a touch panel, button keys, and the like, and receives the operations of a user.

The display unit 16 is, for example, a liquid crystal display and may be integrated with the operating unit 15 as a touch panel display. The display unit 16 is an example of an output unit, and displays an area captured by the imaging unit 11. Furthermore, the display unit 16 displays at least one of a luminance value and a retroreflective coefficient of a target to be measured, and/or at least one determination result relating to an entrance angle and an observation angle, the entrance angle and the observation angle obtained by a method to be described below.

The detecting unit 17 is configured from at least one of a Global Positioning System (GPS) sensor, a gyro sensor, a magnetic compass, an acceleration sensor, a motion sensor, a gravity sensor, or the like mounted internally in the terminal device 1. The detecting unit 17 measures information (geometric information) of a position and an attitude of the detecting unit itself relative to the target subject while the imaging unit 11 is capturing an image. The terminal communication unit 18 is an interface for performing the sending and receiving of data between the terminal device 1 and an external device.

Figure 2A:
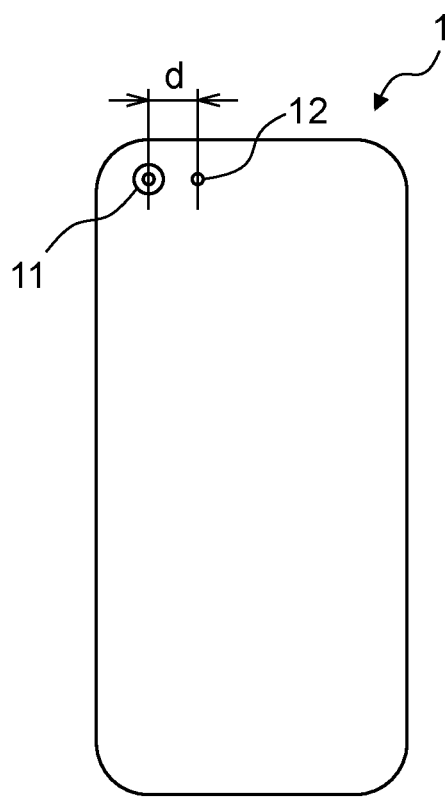
FIG. 2A is a drawing for describing an entrance angle $\theta$ and an observation angle $\varphi$.
Figure 2B:
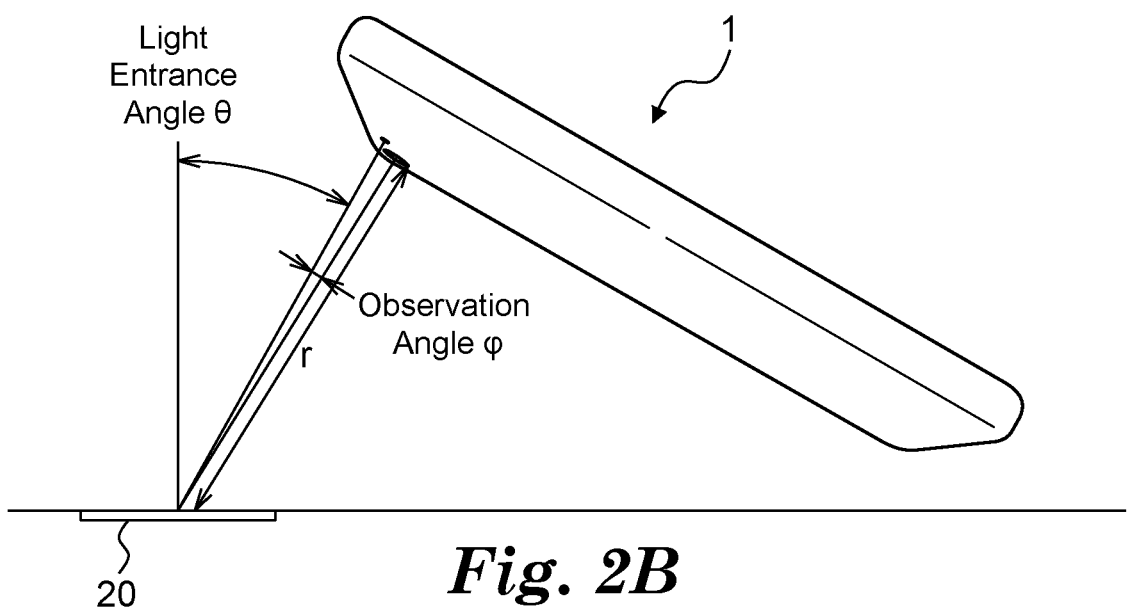
FIG. 2B is a drawing for describing an entrance angle $\theta$ and an observation angle $\varphi$.

FIG. 2A and FIG. 2B are drawings for describing entrance angles θ and observation angles φ. The observation angle φ is determined by a positional relationship between the imaging unit 11, the light emitting unit 12 and the target object, which is a retroreflective material 20. The observation angle φ is calculated based on a distance r from the terminal device 1 to the target object, which is the retroreflective material 20, and a distance d between the lens of the imaging unit 11 and the LED of the light emitting unit 12. The distance d between the imaging unit 11 and the light emitting unit 12 can be measured easily using a ruler and the like. The distance r from the lens of the imaging unit 11 or the LED of the light emitting unit 12 to the retroreflective material 20 is derived using auto focus information from the imaging unit 11. The distance between the light emitting unit 12 and the retroreflective material 20 and the distance between the lens of the imaging unit 11 and the retroreflective material 20 are both nearly identical with mobile terminals where the light source and the lens are placed extremely close to one another, and thus both indicate the distance r in an approximate sense. To be exact, the distance r is derived using a regression curve (calibration curve) between the value of the distance derived from the auto focus information from the imaging unit 11, and an actual value. Furthermore, the observation angle φ is calculated using the following equation.

$$\varphi = \arctan(d/r) \quad (1)$$

The observation angle φ changes based on the distance r from the terminal device 1 to the target object and is thus an amount that corresponds to distance.

The entrance angle θ is an angle between a normal direction of the target object, which is the retroreflective material 20, and the incident direction from which light incidents on the target object. When the retroreflective material 20 is placed horizontally on a table, the entrance angle θ is an incline angle of the terminal device 1 relative to the horizontal direction. On the other hand, when the retroreflective material 20 is attached to a vertical wall surface, the entrance angle θ is an incline angle of the terminal device 1 relative to the vertical direction of the surface. For example, the entrance angle θ is derived by measuring the incline angle of the terminal device 1 relative to a vertical surface or a vertical surface using information from the detecting unit 17. Or, the entrance angle θ may be measured using a separate ruler and/or protractor.

A retroreflective coefficient RA (cd/m²lx) is derived as shown below using an illuminance value I (lx) on the retroreflective material 20 irradiated by the light emitting unit 12 under a specific observation angle φ and entrance angle θ and a luminance value L (cd/m² or nit) of the retroreflection from the retroreflective material 20 at that time.

$$RA = L/I \quad (2)$$

Of these, the luminance value L is derived by a method to be described below using image data of an image captured by the imaging unit 11.

On the other hand, assuming that the light emitting unit 12 is a point light source, the illuminance value I is represented as follows where $L_S$ is (cd/m² or nit) and an effective area A is (m²).

$$I = ((L_S \times A)/r^2)\cos\theta \quad (3)$$

As long as the properties of the LED light source of the light emitting unit 12 are known and the observation angle φ and the entrance angle θ are determined, the illuminance value I can be derived. Therefore, it is not necessary to measure the illuminance value I each time because the correspondence relationship between the type of light source (light emitting unit 12) used, the observation angle φ, the entrance angle θ, and the illuminance value I may be stored in the storage unit 13 in advance and the illuminance value I acquired by making reference thereto. Of course, the illuminance value I and/or the luminance value $L_S$ may be derived using a separate illuminometer and/or luminance meter.

Figure 3:
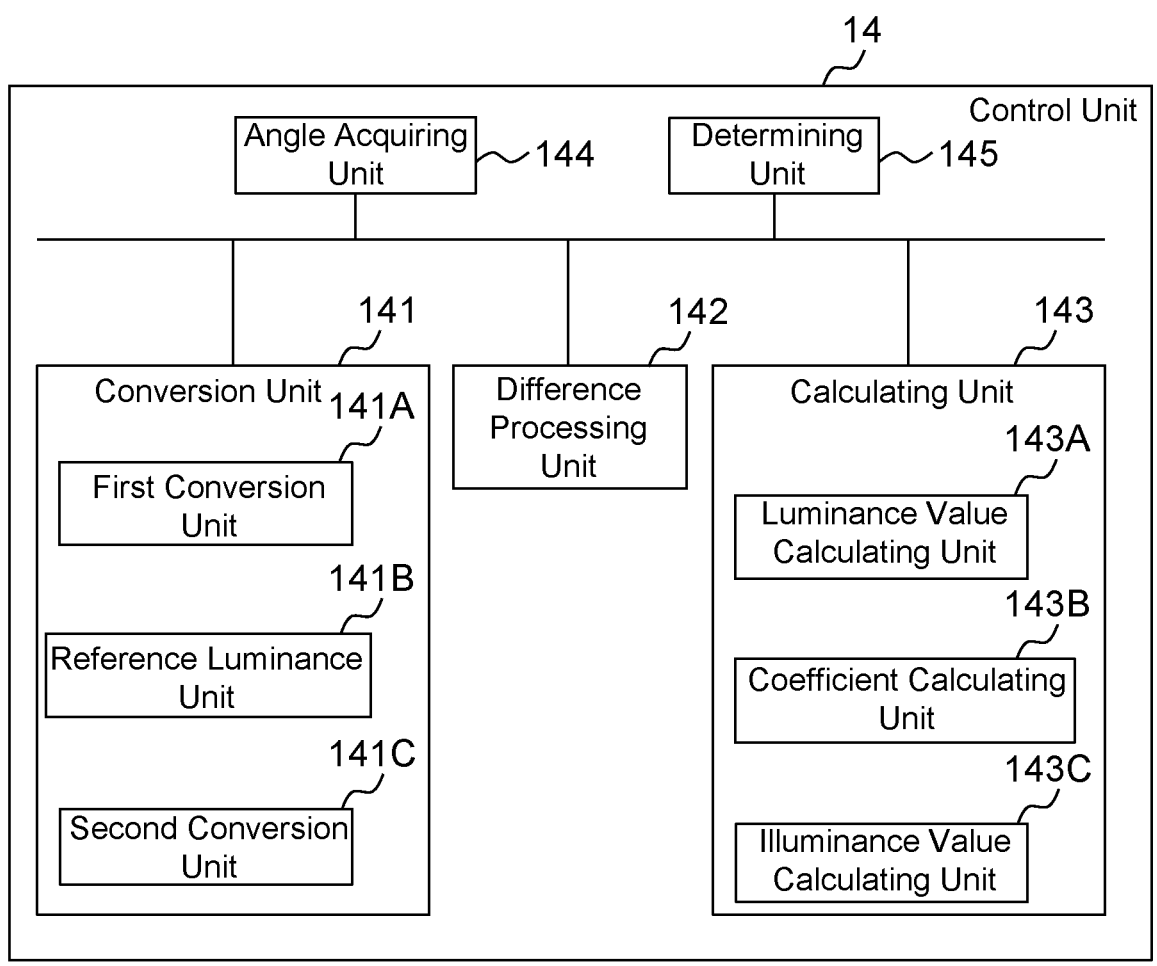
FIG. 3 is a functional block diagram of a control unit 14.

FIG. 3 is a functional block diagram of a control unit 14. The control unit 14 has a conversion unit 141, a difference processing unit 142, a calculating unit 143, an angle acquiring unit 144, and a determining unit 145.

The conversion 141 unit has a first conversion unit 141A, a reference luminance value acquiring unit 141B, and a second conversion unit 141C. The conversion unit 141 acquires image data of an image captured by the imaging unit 11, and then converts the image data to data (a luminance value) that includes photometric information for the target object in an observation angle φ using capture information of the image data. The conversion unit 141 converts image data of a first image, captured in the presence of light emitted for capture, to a first luminance value and, at the same time, converts image data of a second image, captured without the light emitted for capture, to a second luminance value. The first luminance value $L_1$ is the luminance of the retroreflection caused by the light emitted for capture from the light emitting unit 12 and surrounding light while the second luminance value $L_2$ is the luminance of the retroreflection caused by the surrounding light only. The difference $L = L_1 - L_2$ between these two luminance values indicates the luminance of the actual retroreflection caused only by the light emitted for capture by the light emitting unit 12.

The conversion unit 141 converts first image data, acquired by the imaging unit 11 using the light emitted for capture, and second image data, acquired by the imaging unit 11 without using the light emitted for capture, respectively, to luminance values on a linear scale, and then generates two luminance images. Therefore, the conversion unit 141 derives relative luminance values for the first image data and the second image data, respectively, derives reference luminance values for the photographic objects of each of the images, respectively, using the capture information of the imaging unit 11, and then converts the relative luminance values for each of the images to absolute luminance values using the reference luminance values. The absolute luminance value is an amount represented by nit, cd/m² or ftL and the like. For example, at this time, the conversion unit 141 extracts the image capture information of the image data such as the effective aperture value (F value), shutter speed, ISO sensitivity, focal length, and capture distance of the imaging unit 11 from Exif data that accompanies the image data acquired by the imaging unit 11. Furthermore, the conversion unit 141 converts the first image data and the second image data to data that includes the absolute luminance values using the extracted capture information.

Figure 4:
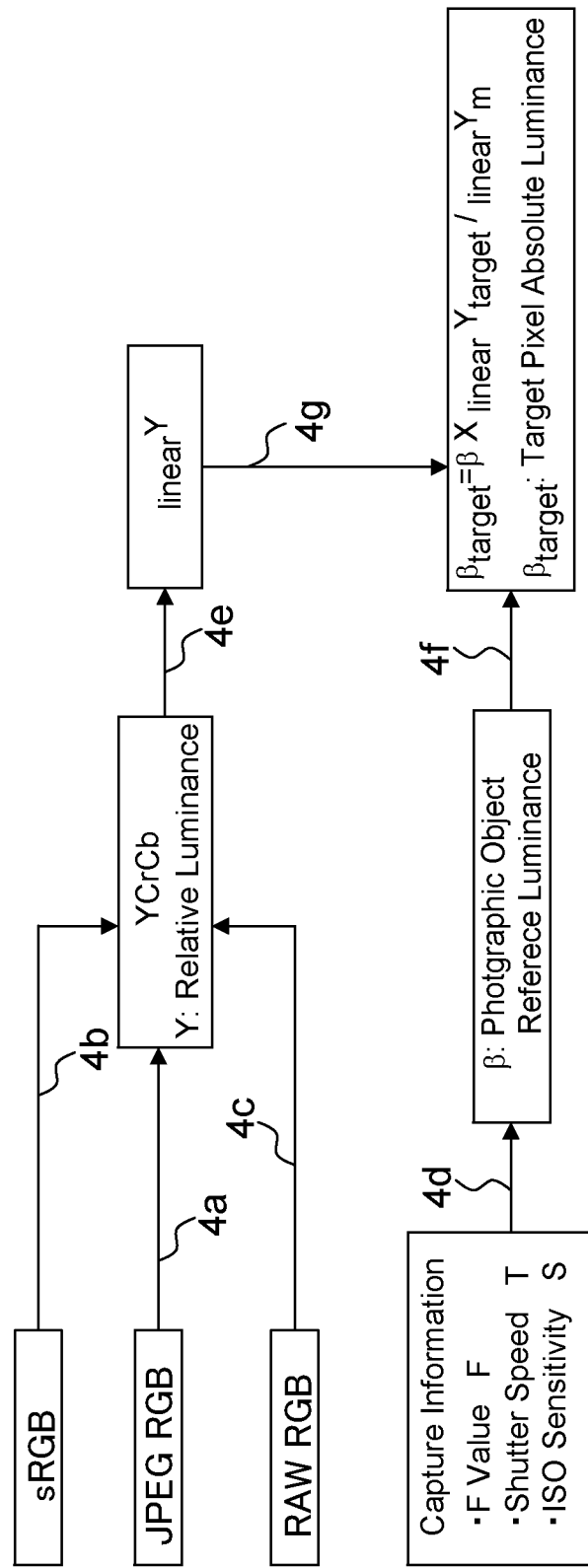
FIG. 4 is a relational diagram of all data used by a conversion unit 141.

FIG. 4 is a relational diagram of all the data used by the conversion unit 141.

The first conversion unit 141A converts JPEG data of an image acquired by the imaging unit 11 to YCrCb data that includes the relative luminance value (arrow 4a). The value of a luminance signal Y is the relative luminance value. At this time, the first conversion unit 141A may convert the JPEG data to YCrCb data in accordance with a conversion table established using the known standard IEC 61966-2-1. Note that, even when the image data is sRGB data, the first conversion unit 141A may still do conversion in accordance with the conversion table established using a known standard (arrow 4b). Furthermore, the first conversion unit 141A may convert RAW data using the conversion table provided by the manufacturer of the imaging unit 11 (arrow 4c).

The reference luminance value acquiring unit 141B uses capture information of image data to derive a reference luminance value β of a photographic object included in an image acquired by the imaging unit 11. The reference luminance value β (cd/m² or nit) is represented by the following equation when an average reflectivity of an entire screen is assumed to be 18%, and when, for the imaging unit 11, the effective aperture value (F value) is F, the shutter speed is T (seconds), and the ISO sensitivity is S.

$$\beta = 10 \times F^2/(k \times S \times T) \quad (4)$$

Where k is a constant and uses, for example, a value such as 0.65 and the like. The reference luminance value acquiring unit 141B uses this equation to calculate the reference luminance value β from the values of the effective aperture value (F value) F, the shutter speed T (seconds), and the ISO sensitivity S (arrow 4d).

In most cases, the F, S, and T capture information is recorded in Exif data that accompanies the RAW data, JPEG data, and the like. Thus, the reference luminance value acquiring unit 141B extracts F, S, and T from the Exif data to calculate the reference luminance value β. User convenience is enhanced by this because the user is thus not required to input the capture information manually. When, on the other hand, the Exif data cannot be used, a user enters the values of F, S, and T through the operating unit 15, and then the reference luminance value acquiring unit 141B acquires the input values.

The second conversion unit 141C converts a relative luminance value Y to an absolute luminance value using the reference luminance value β. At that time, the second conversion unit 141C first derives a linear relative luminance value $_{linear}Y$ by converting the relative luminance value Y to a linear scale (arrow 4e). Furthermore, the second conversion unit 141C converts a linear relative luminance value $_{linear}Y_{target}$ of each pixel of a target to be measured to an absolute luminance value $β_{target}$ using the reference luminance value β calculated by the reference luminance value acquiring unit 141B (arrows 4f and 4g).

In general, the RGB values of pixels displayed on a display are converted to a nonlinear scale using gamma correction to compensate for the nonlinearity of the display. Therefore, in a case where RGB values are used instead of a linear scale, the second conversion unit 141C converts the pixels of the luminance signal Y (nonlinear value) calculated by the first conversion unit 141A to the $_{linear}Y$ of the linear scale through the following equation using, for example, a representative gamma correction value of 2.2.

$$_{linear}Y = Y^{2.2} \quad (5)$$

Doing gamma correction in this way has the advantage of making high speed processing of multiple points at multiple levels easy. Of course, the second conversion unit 141C can, without being limited to equation (5), convert the relative luminance value Y to a linear scale using a unique method for each color space.

If the reference luminance value β is derived when reflectivity is 18%, the second conversion unit 141C calculates the absolute luminance value $β_{target}$ from the linear relative luminance value $_{linear}Y_{target}$ of a target pixel using the following equation.

$$β_{target} = β × _{linear}Y_{target}/_{linear}Y_m \quad (6)$$

Here, $_{linear}Y_m$ is the linear relative luminance value (reference level) when the average reflectivity of the entire screen is assumed to be 18%. In the case of an 8 bit system of 0 to 255, because the reference level becomes 46 (maximum value 255×0.18) due to the definitions of the 2.2 gamma standard and the 18% average reflectivity for the display, $$_{linear}Y_m = 46/255.$$

Whether the capture information of the Exif data is usable or a user manually enters information corresponding thereto, the absolute luminance value $β_{target}$ for the pixel of each coordinate on an image can be derived using the procedure described above from any one of either the sRGB, the RGB of the JPEG data, or the RGB of the RAW data. As long as the absolute luminance values are used, images acquired under different lighting conditions can be compared against one another with greater accuracy. For example, it becomes possible to compare an image captured using normal light to an image captured using fill light such as a flash and the like and to thus determine whether the intensity of the fill light is adequate.

Note that the second conversion unit 141C may perform correction relative to a loss of peripheral light intensity (Vignetting) for the final absolute luminance value R target using a known method such as the so-called cosine fourth power law and the like using angle of view information obtained from the focal length and the size of the image sensor of the imaging unit 11. By this, the accuracy of the absolute luminance value can be enhanced.

Furthermore, the conversion unit 141 may generate the luminance images for the first image data and the second image data based on the relative luminance values of each, respectively, without calculating all the way to the absolute luminance value. In this case, the conversion unit 141 need only include the first conversion unit 141A. The relative luminance value is sufficient in cases where the relative luminance value can be calculated more easily than the absolute luminance value, and accuracy is not required.

The difference processing unit 142 acquires a luminance value of the target object by calculating a difference between a first luminance value and a second luminance value. That is, the difference processing unit 142 calculates the difference between a first luminance value using image data from when capture was being performed in a state where the light emitted for capture was present and a second luminance value using image data from when capture was being performed in a state where the light emitted for capture was not present. This difference may be a per pixel difference, an average value difference for all of the pixels, an average value difference of the pixels of a portion of a capture area, or the like. By this, the effect of the surrounding light is eliminated.

Figure 5C:
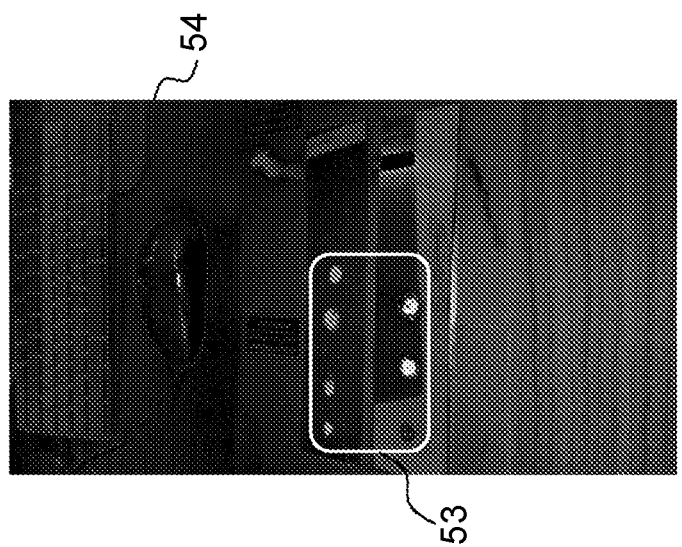
FIG. 5C is a view for describing the difference processing unit 142.
Figure 5B:
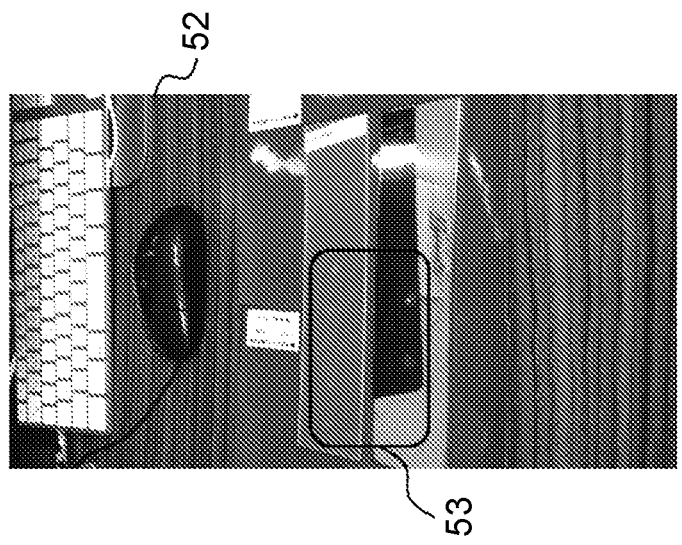
FIG. 5B is a view for describing the difference processing unit 142.
Figure 5A:
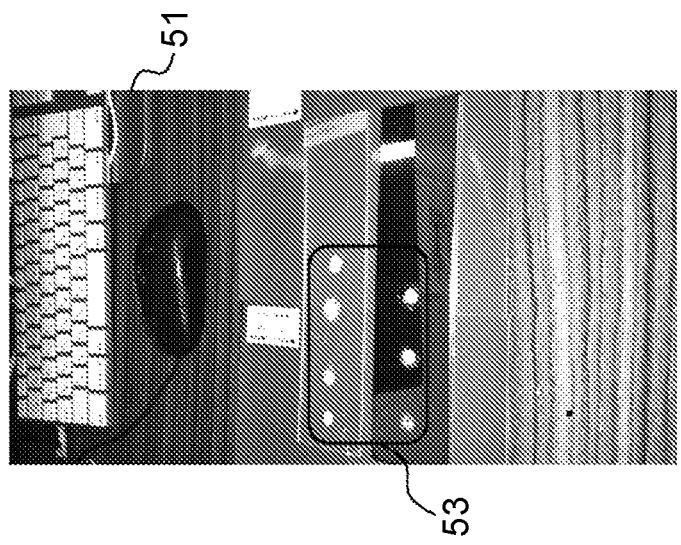
FIG. 5A is a view for describing a difference processing unit 142.

FIG. 5A through FIG. 5C are views for describing the difference processing unit 142.

FIG. 5A is an example of an image 51 captured by the imaging unit 11 using the light emitted for capture by the light emitting unit 12. Furthermore, FIG. 5B is an example of an image 52 captured by the imaging unit 11 without using the light emitted for capture by the light emitting unit 12. In this example, a retroreflective material is applied to seven points inside an area 53 surrounded by a solid line. While the points are almost invisible in the second image 52, where there the light emitted for capture is not present, the seven points can be identified clearly in the first image 51, where the light emitted for capture is present, due to the fact that the light emitted for capture is reflected toward the imaging unit 11 by the retroreflective material.

FIG. 5C is a difference image 54 generated by calculating the luminance value of each pixel of the first image 51 and of the second image 52 and then taking the difference between the luminance values of each pixel. In the difference image 54, the points where the retroreflective material has been applied mainly inside the area 53 can be seen clearly. In this way, the difference processing unit 142 generates a luminance image for the first image data and for the second image data, respectively, and then generates a difference image for the two luminance images.

Note that because it is necessary to align the two images precisely in order to generate the difference image therefor, the imaging unit 11 captures the image that used the light emitted for capture and the image that did not use the light emitted for capture nearly simultaneously using so-called exposure bracketing. Note that a user may capture the aligned first image 51 and second image 52 without using exposure bracketing by using, for example, a tripod or a fixed stand to fix the terminal device 1 in place.

The difference processing unit 142 calculates the difference between the first luminance value based on the first image data and the second luminance value based on the second image data converted by the conversion unit 141, on, for example, a pixel by pixel basis to generate a difference image like that illustrated in FIG. 5C. The first luminance value and the second luminance value may be either absolute luminance values or relative luminance values. For areas where the luminance value changes very little regardless of the presence or absence of the light emitted for capture, even in cases where bright areas not related to the retroreflective material are included within an image, this can largely be removed by capturing a difference image.

The calculating unit 143 has a luminance value calculating unit 143A, a coefficient calculating unit 143B, and an illuminance value calculating unit 143C.

The luminance value calculating unit 143A calculates the average values of the relative luminance values or the absolute luminance values converted by the conversion unit 141 for the pixels of a target area.

Note that the luminance value calculating unit 143A may eliminate the effect of surrounding light by correcting the luminance value of the target object based on the luminance value of portions other than the target object obtained from image data of an image that includes the target object and portions other than the target object such as a wall surface or the like. For example, when the luminance value of the portions other than the target object are outside a range established in advance, that is, in a case where the data of the luminance value is saturated such that the entire image is too bright or too dark, the luminance value calculating unit 143A may make corrections so as to fit the luminance value of the entire image within the range established in advance by using a fixed degree of magnification to make the luminance value of the entire image either smaller or larger.

The coefficient calculating unit 143B calculates the value of the retroreflective coefficient of the target object based on the illuminance value I and the luminance value L of the target object when the observation angle φ and the entrance angle θ are both included within a range of reference established in advance. The coefficient calculating unit 143B displays the value of the calculated retroreflective coefficient on the display unit 16.

The illuminance value calculating unit 143C calculates the illuminance value of the target object based on, for example, the luminance value of the retroreflective material from when light from the light source was being irradiated on a retroreflective material, for which the value of the retroreflective coefficient is known, in order to calibrate the illuminance value. In a case where a retroreflective material used for reference, where the value of the retroreflective coefficient is $RA_0$, can be used, the illuminance value I from the light emitting unit 12 is back calculated as shown below using a luminance value $L_0$ calculated for the retroreflective material used for reference by the luminance value calculating unit 143A.

$$I = L_0/RA_0 (\text{lx}) \quad (7)$$

Once the illuminance value I is obtained, the retroreflective coefficient RA of the target object is calculated as follows using a luminance value L calculated by the luminance value calculating unit 143A for the retroreflective material, which is the target to be measured.

$$RA = L/I (\text{cd/m}^2 \text{lx or nit/lx}) \quad (8)$$

As long as the retroreflective material used for reference can be used, the illuminance value can easily be determined and/or calibrated without using a illuminometer by using the value of a known retroreflective coefficient that will serve as a reference. In a case where the calculated illuminance value and the illuminance value stored in the storage unit 13 are different, the illuminance value calculating unit 143C updates the illuminance value stored in the storage unit 13 using the calculated illuminance value.

The angle acquiring unit 144 acquires the observation angle φ for the distance r from the imaging unit 11 or the light emitting unit 12 to the retroreflective material 20 and the distance d between the imaging unit 11 and the light emitting unit 12, which were derived using the autofocus information of the imaging unit 11. The angle acquiring unit 144 functions as an observation angle acquiring unit in conjunction with the auto focus function of the imaging unit 11. Furthermore, the angle acquiring unit 144 acquires the value of the entrance angle θ, at which the light emitted for capture is incident on the target object, based on incline angle information for the terminal device 1 calculated by the detecting unit 17. The angle acquiring unit 144 functions as an entrance angle acquiring unit in conjunction with the detecting unit 17. The angle acquiring unit 144 displays the values of the acquired observation angle φ and entrance angle θ on the display unit 16.

The determining unit 145 references the range of reference information for the observation angle φ and entrance angle θ stored in the storage unit 13, and determines whether the values of the observation angle φ and entrance angle θ acquired by the angle acquiring unit 144 are both included within the range of reference. Because the sizes of the observation angle φ and entrance angle θ established from a standard will differ based on the type of target object captured, the determining unit 145 determines whether the values of the observation angle φ and entrance angle θ acquired by the angle acquiring unit 144 are included within the range of reference for the target object to be measured.

The determining unit 145 notifies the user of the determination results by, for example, displaying the results on the display unit 16. In this case, the determining unit 145 may change the display mode of the display unit 16 based on, for example, when the determining unit determines the values of the observation angle φ and entrance angle θ are within the range of reference versus when the unit determines the values of the observation angle φ and/or entrance angle θ are not within the range of reference. Or, the determining unit 145 may notify the user of the determination results by methods such as causing an LED provided separately from the light emitting unit 12 to blink, changing the color of the LED, driving an internally mounted vibration function, generating a sound using an internally mounted speaker, or the like.

In order to measure the retroreflective coefficient, the measuring unit and the light source for emitting light for capture must be arranged according to an observation angle φ and entrance angle θ established arbitrarily or by using a standard. However, manually holding the terminal device 1 with precision during capture places a significant burden on users. Thus, the imaging unit 11 may automatically release the shutter to capture the image of the target object, without regard to an operation by a user, whenever the determining unit 145 determines that the values of the observation angle φ and entrance angle θ are both included within the range of reference. Thanks to this automatic shutter function, all a user need do is move the terminal device 1 within the target range without the need to precisely align the angle of the terminal device 1 by hand, thus making measurement easy.

FIG. 6A is a table showing examples of observation angles φ and entrance angles θ that determine a range of reference. The storage unit 13 stores correspondence relationships between observation angles φ and entrance angles θ, like, for example, those shown in FIG. 6A, needed to determine ranges of reference corresponding to the type of the target object. The observation angles φ and entrance angles θ shown in FIG. 6A are values recommended by ANSI/ISEA 107-2010 for measuring retroreflective coefficients. Because it is difficult to actually align angles to specified values precisely, the range of reference is set in a fixed ranged centered on specified values. For example, if the entrance angle θ is five degrees, five degrees±one degree is set as the range of reference. The fact that there is a margin in the value of the angles is shown in FIG. 6A by the symbols "±Δφ" and "±Δθ." For example, in a case where the distance d between the imaging unit 11 and the light emitting unit 12 is about 1 cm, the condition that the observation angle φ be 12 minutes (=0.2 degrees) corresponds to capturing the target object from about 3 m away.

In a case where the distance d is about 1 cm and the distance r is, for example, an extremely short value such as 1 m or less and the like, the effect of diffused light on the surface on which the target object is placed becomes significant. However, as long as the position is adequately far away, such as 1 m or more and the like where diffused light decays, specular reflection caused by the retroreflective material becomes dominant and the reflected light becomes parallel light, and thus the luminance value L will remain largely unchanged even if the observation angle φ (the distance r from the target object) is changed somewhat. It has been confirmed, through actual measurements, that as long as the position is at least 1 m away from the target object, the measured value changes little within a range of around, for example, 1 to 5 m. Therefore, by keeping a fixed margin in the observation angle φ, the tolerance for the distance r between the target object and the terminal device 1 becomes approximately 1 to 3 m.

FIG. 6B is a table showing correspondence relationships between types of light sources, and the observation angles φ, entrance angles θ, and illuminance values I of the target object. The storage unit 13 also stores correspondence relationships between light source types and observation angles φ, entrance angles θ, and target object illuminance values I like those shown in FIG. 6B. The coefficient calculating unit 143B references these correspondence relationships in the storage unit 13, and then calculates the retroreflective coefficient RA for the target object using the obtained illuminance value I and the luminance value L calculated by the luminance value calculating unit 143A.

Note that the light source for emitting light for capture may be a device that is physically separate from the imaging unit 11. As long as the illuminance values that correspond to the light sources to be used during capture are stored in the storage unit 13 in advance, as in FIG. 6B, the retroreflective coefficient can be calculated even from an image captured using a light source other than the light emitting unit 12.

Figure 7:
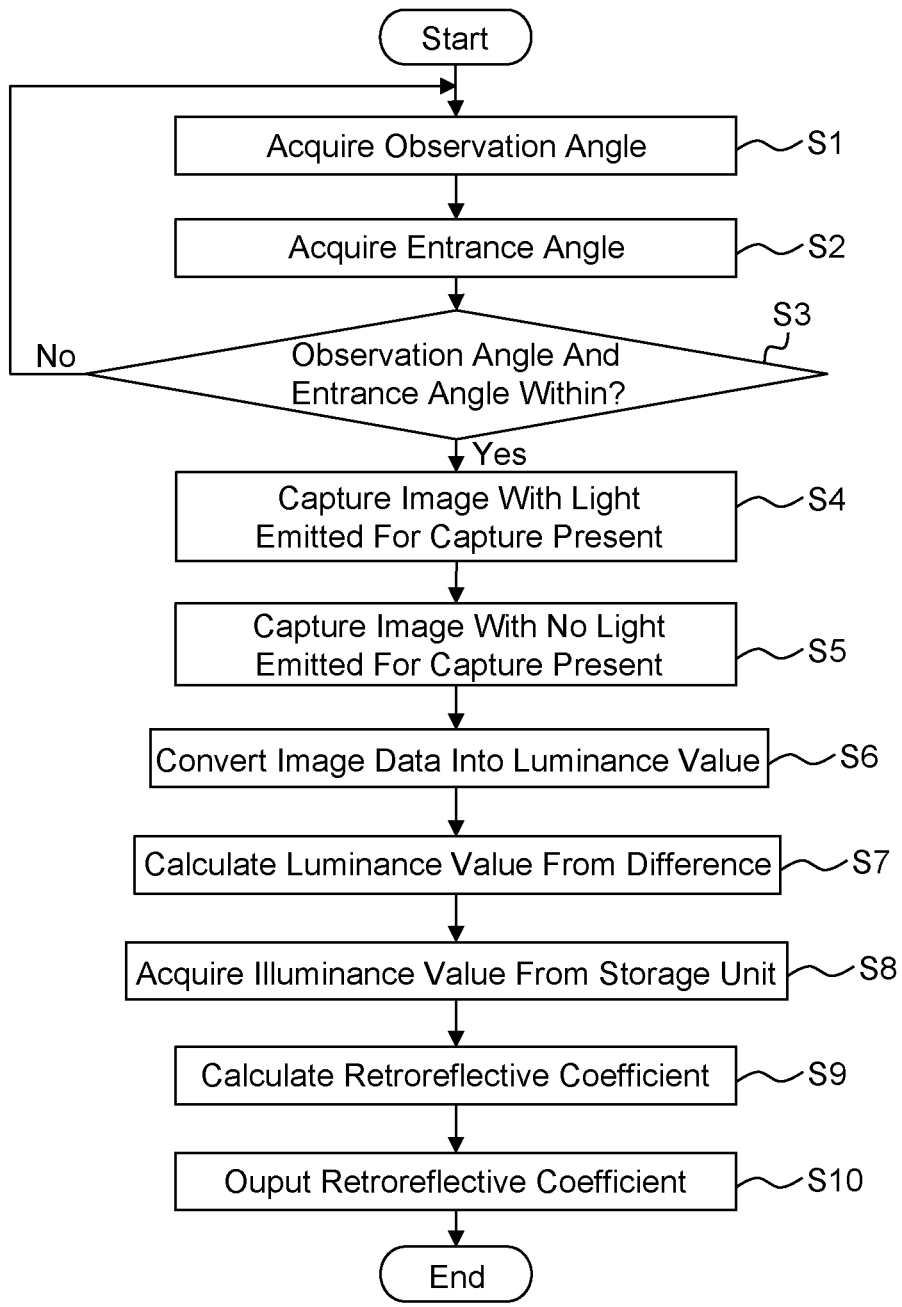
FIG. 7 is a flow chart illustrating an operational example for the terminal device 1.

FIG. 7 is a flow chart illustrating an operational example for the terminal device 1. The steps of the process in FIG. 7 are executed by the control unit 14 in cooperation with each element of the terminal device 1 based on a program stored in the storage unit 13.

First, the angle acquiring unit 144 of the control unit 14 acquires the observation angle determined by the positional relationship between the light source for emitting light for capture and the target object (step S1). At this time, the angle acquiring unit 144 acquires the observation angle φ for the distance r from the imaging unit 11 or the light emitting unit 12 to the retroreflective material 20, which was derived using the autofocus information of the imaging unit 11, and the distance d between the imaging unit 11 and the light emitting unit 12. Furthermore, the angle acquiring unit 144 acquires the value of the entrance angle θ, at which the light emitted for capture is incident on the target object, based on incline angle information for the terminal device 1 calculated by the detecting unit 17 (step S2).

Furthermore, the determining unit 145 of the control unit 14 references the range of reference information for the observation angle φ and entrance angle θ stored in the storage unit 13, and determines whether the values of the observation angle φ and entrance angle θ acquired by the angle acquiring unit 144, which was acquired in step S1 and step S2, are both included within the range of reference (step S3). As occasion calls, the angle acquiring unit 144 and the determining unit 145 will display the observation angle φ and entrance angle θ, along with the determination results for each, on, for example, the display unit 16. The angle acquiring unit 144 and the determining unit 145 repeat the processing in steps S1 through S3 until the observation angle φ and entrance angle θ are included within the range of reference.

Furthermore, if the observation angle φ and entrance angle θ are determined to be included within the range of reference (Yes at step S3), the control unit 14 captures, in the imaging unit 11 and the light emitting unit 12, the first image of the target object using the light emitted for capture (step S4), and then, almost at the same time, captures the second image of the target object without using the light emitted for capture (step S5).

Next, the conversion unit 141 of the control unit 14 converts the image data of the first image, captured in step S4, to the first luminance value and, at the same time, converts the image data of the second image, captured in step S5, to the second luminance value (step S6). At that time, the conversion unit 141 converts each piece of image data to a luminance value on a linear scale to generate two luminance images. These luminance values may be the relative luminance values obtained by the first conversion unit 141A, or they may be the absolute luminance values obtained by the second conversion unit 141C. Furthermore, the difference processing unit 142 of the control unit 14 acquires the luminance value of the target object by calculating the difference between the first luminance value and the second luminance value converted in step S6 (step S7).

Furthermore, the calculating unit 143 of the control unit 14 acquires the illuminance value corresponding to the observation angle φ and entrance angle θ at the time of capture in steps S4 and S5 from the storage unit 13 (step S8). Next, the calculating unit 143 calculates the value of the retroreflective coefficient of the target object based on the luminance value of the target object acquired in step S7 and the illuminance value acquired in step S8 (step S9). Finally, the calculating unit 143 displays the value of the retroreflective coefficient calculated in step S9 on the display unit 16 (step S10). This ends the process in FIG. 7.

Figure 8A:
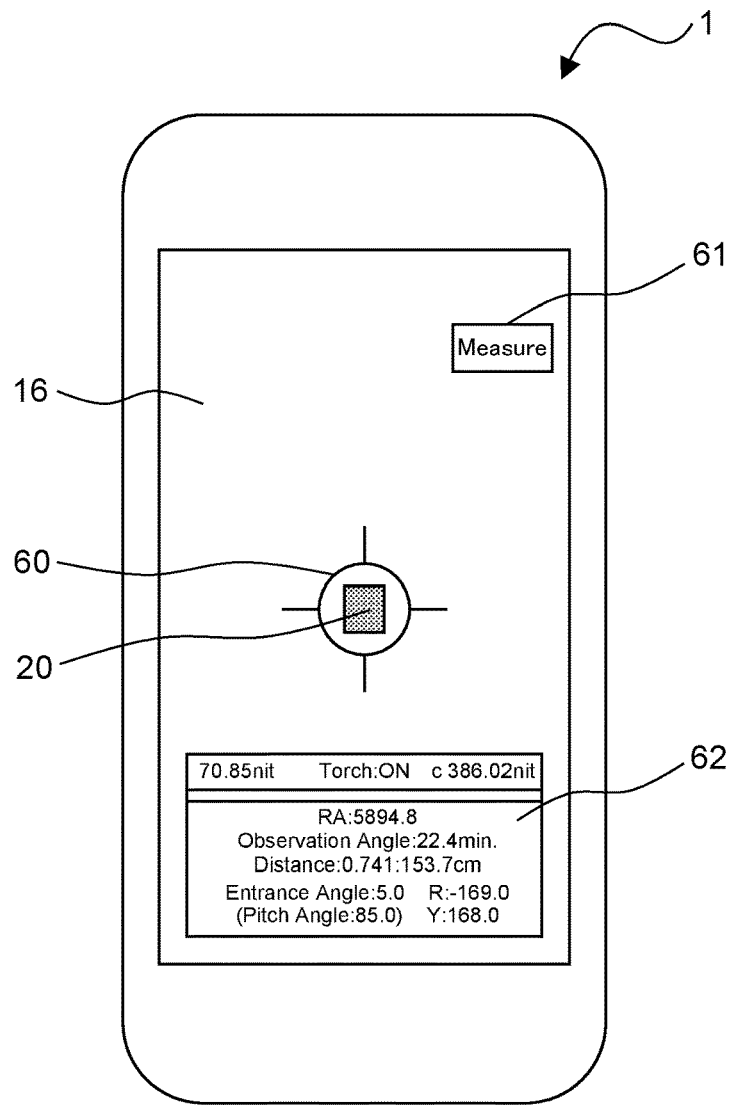
FIG. 8A is a drawing illustrating an example of the screen displayed on a display unit 16 during capture.
Figure 8B:
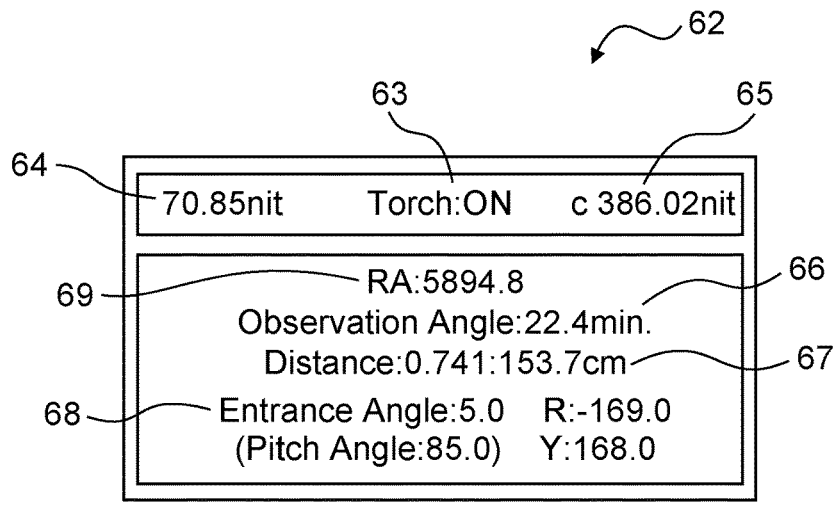
FIG. 8B is a partially enlarged view of FIG. 8A.

FIG. 8A is a drawing illustrating an example of the screen displayed on the display unit 16 during capture. Furthermore, FIG. 8B is an enlarged view of FIG. 8A. During capture, the target object captured by the imaging unit 11, and an area, which is the background of the target object, other than the target object are displayed on the display unit 16. Furthermore, in addition to the display of the field of view of the imaging unit 11, a round symbol 60 is displayed in the middle of the screen, a measure button 61 is displayed in the upper right of the screen, and a notification area 62 is displayed on the bottom of the screen on the display unit 16.

The round symbol 60 is for notifying the user of the area of a target to be measured having the retroreflective coefficient. The measure button 61 is a button for starting the measurement, and, when a user presses this button, the two images, with and without light emitted for capture, are captured, and then the retroreflective coefficient is calculated and displayed in the notification area 62. Furthermore, if the user presses the measure button 61 when the automatic shutter function described above is set to function, the shutter of the imaging unit 11 will automatically release whenever the observation angle φ and entrance angle θ meet the specified requirements, and then the retroreflective coefficient is calculated from the image data captured at that time. The notification area 62 is an area for displaying the values of the observation angle φ, entrance angle θ, retroreflective coefficient, and the like.

The display contents of the notification area 62 are described below. Reference numeral 63 indicates whether the light emitting unit 12 (torch) is lit (ON) or not lit (OFF). By pressing the reference numeral 63, the user can switch the light emitting unit 12 on and off.

The luminance value for reference numeral 64 in the upper left is the average luminance in the vicinity of the area surrounded by the symbol 60 in the middle of the field of view of the imaging unit 11. In the example illustrated in the figures, because the retroreflective material 20, which is the target object, and portions other than the material are included within the circle of the symbol 60, the luminance value for reference numeral 64 basically corresponds to the level of ambient light. On the other hand, the luminance value for reference numeral 65 in the upper right is the average luminance of several pixels in the center area within the circle of symbol 60. If correct calculation is impossible because these luminance values are saturated and the like, the user may be notified that there is an abnormality in the numbers by, for example, changing the display color from green to red, and the like.

Reference numeral 66 is the value of the observation angle acquired by the angle acquiring unit 144. Reference numeral 67 is the distance r between the terminal device 1 and the retroreflective material 20 calculated using a regression curve (calibration curve) in the control unit 14 from the auto focus information of the imaging unit 11. Reference numeral 68 indicates the values of the entrance angle and pitch angle calculated based on information from the detecting unit 17. The sum of the entrance angle and the pitch angle is 90 degrees, and the angles are in a relationship where one is a complementary angle of the other. Furthermore, reference numeral 69 is the value of the final retroreflective coefficient RA calculated by the coefficient calculating unit 143B using the method described above.

Figure 8C:
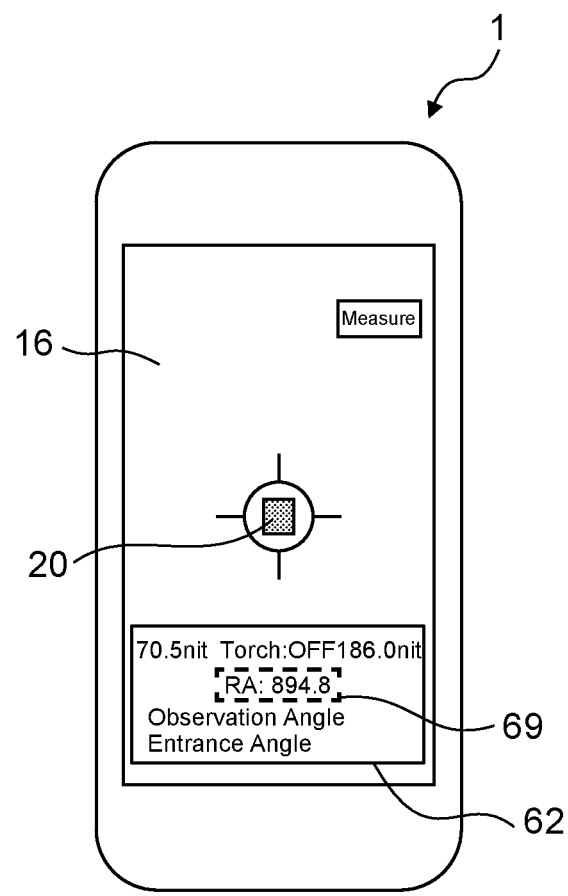
FIG. 8C is a drawing illustrating a display example of a value for a calculated retroreflective coefficient.
Figure 8D:
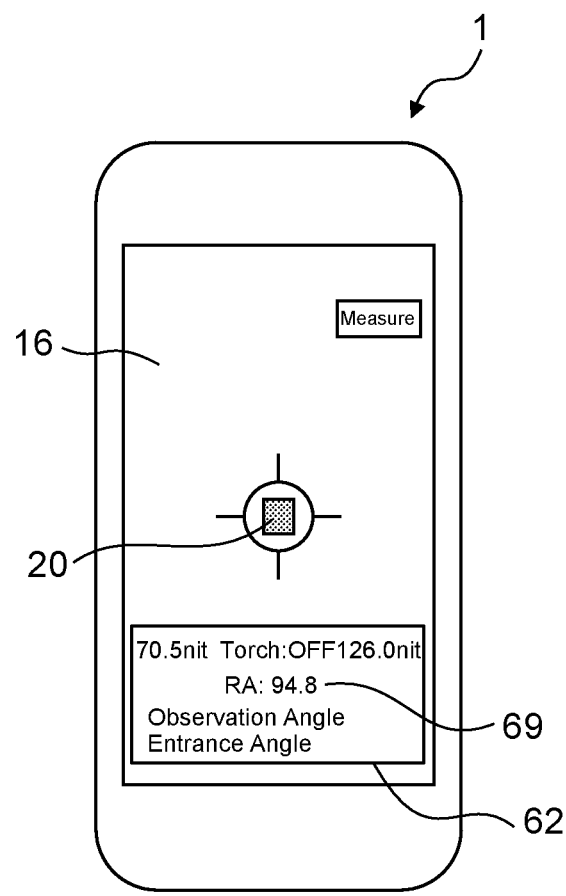
FIG. 8D is a drawing illustrating a display example of a value for a calculated retroreflective coefficient.

FIG. 8C and FIG. 8D are drawings illustrating a display example of a value for a calculated retroreflective coefficient. The control unit 14 determines whether the value calculated for the retroreflective coefficient is included within a range of reference established in advance, and may display the calculated value in different ways based on the resulting determination results, as illustrated in FIG. 8C and FIG. 8D. For example, when the calculated value is within the range of reference, the value may be displayed with emphasis given thereto, conversely, the value may likewise be displayed with emphasis given thereto when the calculated value is outside the range of reference. In the examples illustrated in the figure, the calculated value "894.8" of the retroreflective coefficient (RA) illustrated by the reference numeral 69 in FIG. 8C is within the range of reference while the calculated value "94.8" illustrated by the reference numeral 69 in FIG. D is outside the range of reference, and the calculated valve that is within the range of reference is displayed with emphasis given thereto. For convenience, these different display modes are indicated in FIG. 8C and FIG. 8D by the presence or absence of a frame made up of a dotted line. Or, the control unit 14 may display the calculated value in green when the value is within the range of reference, and in red when the value is not within the range of reference. By this, it becomes possible for the user to easily determine the product lifetime of the target object to be measured.

In order to determine the calculated value of the retroreflective coefficient, the control unit 14 sets a threshold for the retroreflective coefficient in advance and thus, for example, as long as the value calculated by the coefficient calculating unit 143B meets or exceeds the threshold, the value is determined to be within the range of reference, while when the calculated value is below the threshold, the value is determined to be outside the range of reference. For example, with $cd/m^2 lx$ as the unit, when the threshold for the retroreflective coefficient is set at 200, a value equal to or greater than 200 is within the range of reference while a value of, for example, 180, 160, 140, 120, 100, 80, 60, or 40 or less is outside the range of reference. Furthermore, for example, when the threshold for the retroreflective coefficient is set at 100, a value equal to or greater than 200, 180, 160, 140, 120, or 100 is within the range of reference while a value of, for example, 80, 60, or 40 or less is outside the range of reference.

Or, the control unit 14 may set two thresholds, a first threshold and a second threshold that is lower than the first threshold, as the thresholds for the retroreflective coefficient. In this case, the control unit 14 determines values calculated by the coefficient calculating unit 143B that are equal to or greater than the first threshold to be within the range of reference, calculated values that are below the first threshold but equal to or greater than the second threshold to be within an intermediate range, and calculated values that are below the second threshold to be out of the range of reference. For example, with $cd/m^2 lx$ as the unit, when the first threshold is set to 180 and the second threshold is set to 60, values that are equal to or greater than 180 are within the range of reference, values that are below 180 but greater than or equal to 60 are within the intermediate range, and values that are below 60 are outside the range of reference. Calculated values of the retroreflective coefficient that are within the range of reference indicate that the retroreflective performance of the target object is adequate, calculated values that are within the intermediate range indicate that the retroreflective performance of the target object is dropping and it is almost time to replace the product, and calculated values that are outside the range of reference indicate that the retroreflective performance of the target object is inadequate and that the product needs to be replaced.

Furthermore, the coefficient calculating unit 143B may calculate and display the retroreflective coefficient even when the observation angle φ and entrance angle θ do meet the conditions of the specifications therefor (or arbitrary set conditions). In this case, the value displayed for reference numeral 69 is a provisional number, however, because the value of the retroreflective coefficient can be considered to be far outside the range of reference, even if the measurement conditions are not strictly met, when it is clear that material has exceeded the product lifetime thereof, this allows the user to be notified of simple measurement results.

Furthermore, the terminal device 1 may have, as an accessory, one or a plurality of reference target objects for which the values of the retroreflective coefficients of retroreflective material used for reference, are already known. In this case, the terminal device 1 may image the target object to be measured together with the reference target object. Since, by doing this, the operator can detect differences in the strengths of the retroreflection of target areas using the light emitted for capture, this is convenient for occasions when users wish simply to perceive the magnitude relationships between retroreflective coefficients.

Figure 9:
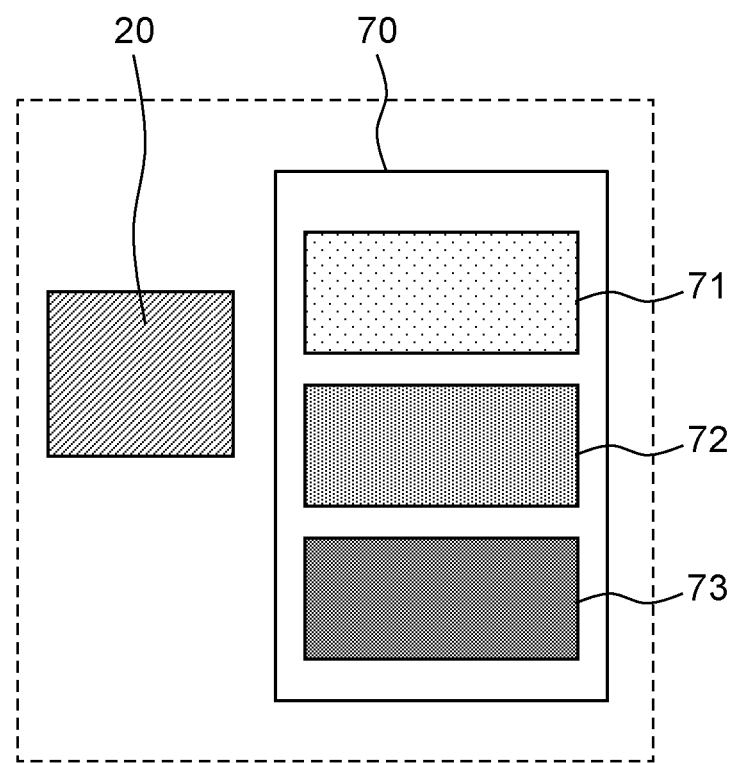
FIG. 9 is a drawing for describing a reference target object.

FIG. 9 is a drawing for describing a reference target object. In FIG. 9, reference numeral 20 illustrates a retroreflective material that is a target object to be measured, and reference numeral 70 illustrates a reference target object. The reference target object 70 includes three retroreflective areas 71 through 73 for which the retroreflective coefficients are known. For example, retroreflective materials where the values of the retroreflective coefficients are variously within a range of reference, within an intermediate range, and outside the range of reference, respectively, are arranged in the retroreflective areas 71 through 73.

For example, in this case, the calculating unit 143 may calculate the value of the retroreflective coefficient of the retroreflective material 20, which is a target object to be measured, from an image where the retroreflective material 20 and the reference target object 70 have been captured together, and then determine which of the values of the retroreflective coefficients of the retroreflective areas 71 through 73 the calculated value is closest to. Or, the calculating unit 143 may, for example, calculate the luminance values for the area of the retroreflective material 20 and the retroreflective areas 71 through 73 from an image where the retroreflective material 20 and the reference target object 70 have been captured together before calculating the retroreflective coefficient for the retroreflective material 20. In this case, the calculating unit 143 may determine, by the magnitude relationships between the luminance values, which of the values of the retroreflective coefficients of the retroreflective areas 71 through 73 the value of the retroreflective coefficient of the retroreflective material 20 is closest to. In this way, the calculating unit 143 may perform calculation using the feature values of the values of the retroreflective coefficients and the luminance values of the retroreflective areas 71 through 73.

It is preferable that the retroreflective areas 71 through 73 be arranged on the reference target object 70 in a pattern established in advance. By this, the control unit 14 can recognize the positions of the retroreflective areas 71 through 73 using known image processing techniques by the overall shape of the reference target object 70 and the shapes of the retroreflective areas 71 through 73, and can thus perform calculation easily using the feature values thereof.

While the example illustrated in the figures uses three retroreflective areas, the number of retroreflective areas included in the reference target object may be one, or two, or four or more. For example, when one retroreflective area is included in the reference target object, it is preferable that the retroreflective coefficient of the area be a threshold that illustrates the boundary of the range of reference for the retroreflective coefficient. Furthermore, when two retroreflective areas are included in the reference target object, it is preferable that the retroreflective coefficients of these areas be a first threshold that illustrates a boundary within the range of reference and the intermediate range of the retroreflective coefficient described above, and a second threshold that illustrates a boundary outside the range of reference and within the intermediate range of the retroreflective coefficient. In this way, it is preferable that the values of the retroreflective coefficients in a plurality of retroreflective areas be different from one another.

Figure 10A:
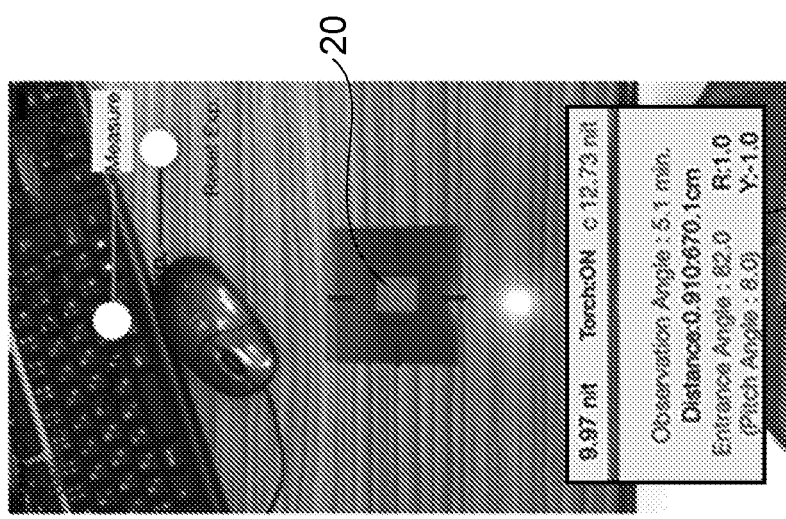
FIG. 10A is a view illustrating an example of the screen displayed on a display unit 16 during capture.
Figure 10B:
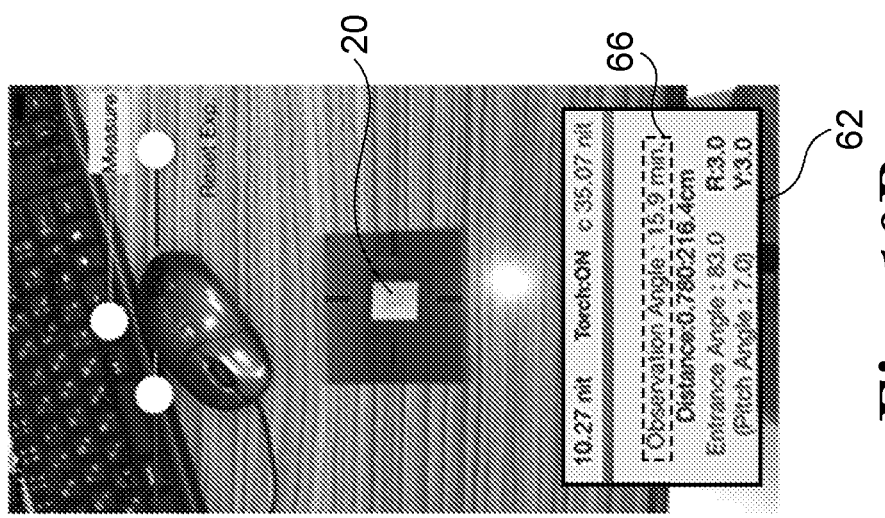
FIG. 10B is a view illustrating an example of the screen displayed on the display unit 16 during capture.
Figure 10C:
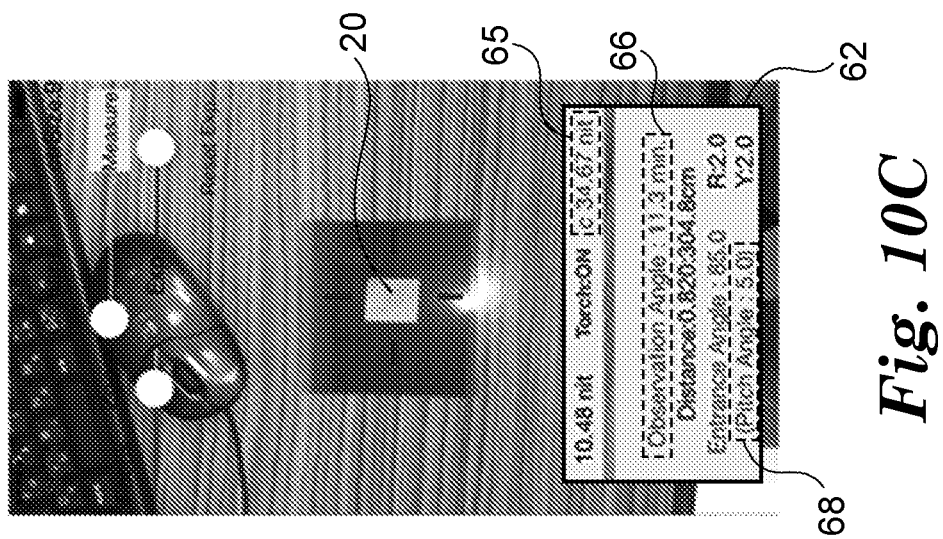
FIG. 10C is a view illustrating an example of the screen displayed on the display unit 16 during capture.

FIG. 10A through FIG. 10C are views illustrating an example of the screen displayed on the display unit 16 during capture. These views illustrate, in a state where the light emitting unit 12 has been lit, changes in the display of the notification area 62 when the position and angle of the terminal device 1 have been changed relative to the retroreflective material 20, which is the target object.

FIG. 10A illustrates a state where both the observation angle (5.1 minutes) and the entrance angle (82 degrees) are outside a range of reference established in advance. FIG. 10B illustrates a state where the terminal device 1 has been moved from the state in FIG. 10A to bring the observation angle (15.9 minutes) of reference numeral 66 within the range of reference. At this time, the display mode for the value of the observation angle changes through, for example, a change in color where the text color changes from red to green or the like, to notify the user of this state. For convenience, these changes in display mode are indicated in FIG. 10B and FIG. 10C by frames made up of a dotted line.

FIG. 10C illustrates a state where the terminal device 1 has been further moved from the state in FIG. 10B to bring both the observation angle (11.3 minutes) of reference numeral 66 and the pitch angle (5.0 degrees) of reference numeral 68 within the range of reference. At this time as well, the display modes for the values for the observation angle and the pitch angle also change such that the text color therefor changes to green or the like. The example illustrated in the figures arranges the retroreflective material 20 horizontally, and while the 85.0 degrees of the entrance angle is outside the range of reference, the figures illustrate that the 5.0 degrees of pitch angle is within the range of reference. Note that in FIG. 10C, the display mode for the data of the luminance value of the measurement area displayed for reference numeral 66 in the top right of the notification area 62 has also changed, which indicates that a luminance value (34.67 nit) not saturated in data has been obtained in FIG. 10C for the first time.

From FIG. 10C, the user can perceive that the observation angle and the pitch angle (entrance angle) are both included within the range of reference of $\varphi \pm \Delta\varphi$ and $\theta \pm \Delta\theta$. Accordingly, if the user presses the measure button 61 at this time, an image of the retroreflective material 20 can be captured by the terminal device 1 and a retroreflective coefficient derived therefor. If the automatic shutter function described above is set to operate, the image of the retroreflective material 20 is captured and the retroreflective coefficient therefor derived automatically when the state in FIG. 10C is reached. If a user utilizes the automatic shutter function, it becomes possible to measure the retroreflective coefficient simply by moving the terminal device 1, without giving any consideration to the current observation angle and entrance angle.

If the distance d between the lens of the imaging unit 11 and the LED of the light emitting unit 12 is 10.0 mm, the distance r from the terminal device 1 to the target object should be 2866 mm when, for example, the observation angle is set to 12 minutes. However, it is, in fact, easier to measure from a position that is closer to the target object. In this case, if the distance d between the light source and the lens is made shorter, the distance r from the terminal device 1 to the target object can be made shorter without changing the size of the observation angle. For example, an optical element such as a prism and the like can be used to shorten the distance d between the light source and the lens.

Figure 11:
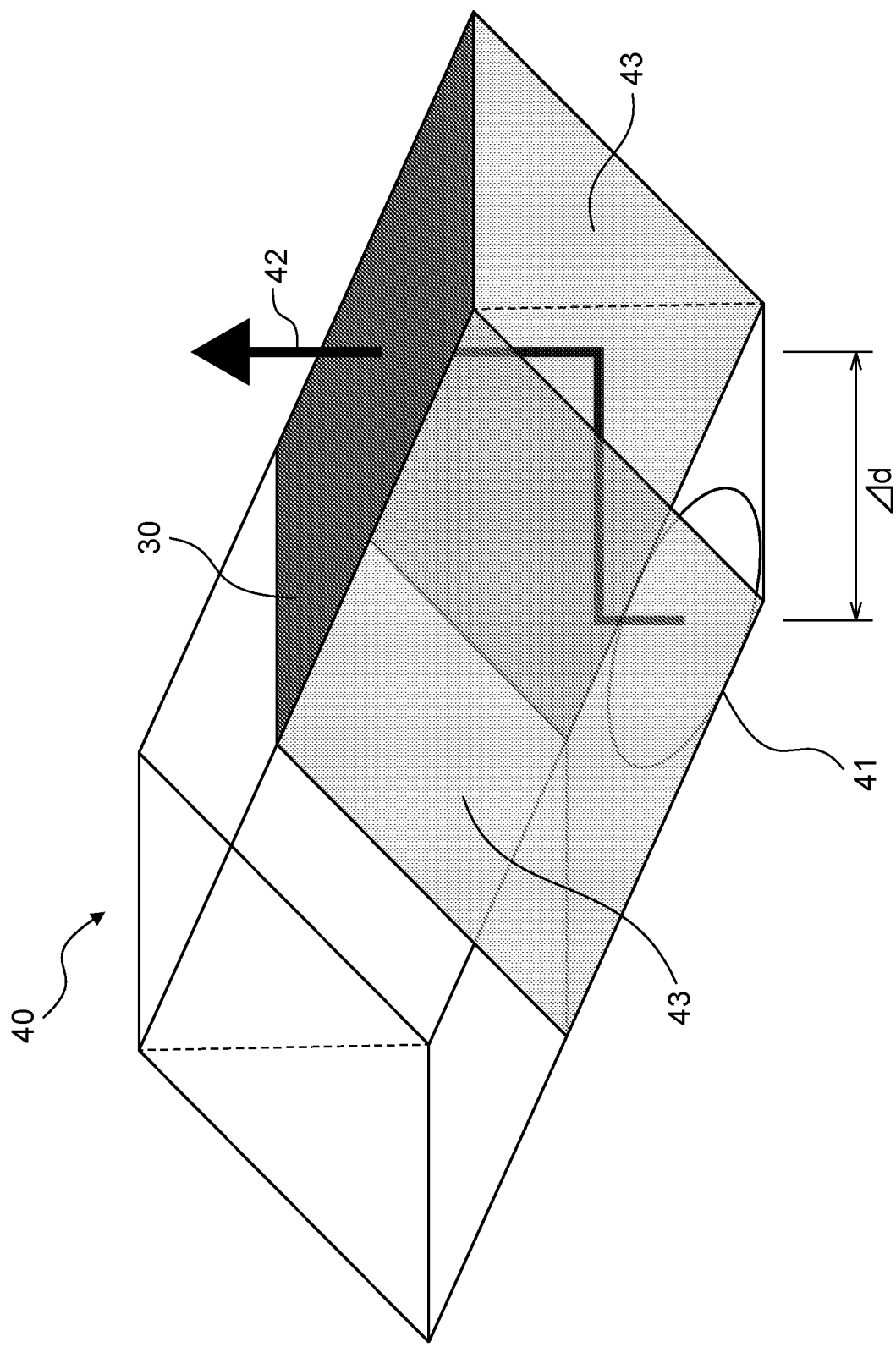
FIG. 11 is a perspective view illustrating an example of a filter 30 and a prism 40.

FIG. 11 is a perspective view illustrating an example of a filter 30 and a prism 40. The prism 40 deflects the light path of the light from the light source and thus adjusts the size of the observation angle. In the example illustrated in the figure, the light from the light emitting unit 12 incidents from an area 41 on the bottom surface of the prism 40. A black film 43 is affixed to the side surfaces of the prism 40, and a beam 42 of incident light is refracted twice by the two side surfaces of the prism 40 and is thus emitted outside from the top surface of the prism 40. These two refractions cause the position of an optical axis to move horizontally from before incidence to after emission by exactly $\Delta d$. Accordingly, attaching this kind of prism 40 to the light emitting unit 12 of the terminal device 1 makes it possible to shorten the distance d between the light source and the lens.

Furthermore, a dimming (ND) filter 30 is affixed to the top surface of the prism 40 in FIG. 11. Because the light from the light emitting unit 12, which is the LED light source of the terminal device 1, is especially bright, this type of filter 30 may also be used to reduce the intensity of the light emitted for capture when measurement of the retroreflective coefficient is being performed from a close distance.

As has been described above, the terminal device 1 acquires an entrance angle and an observation angle that show a positional relationship between the terminal device itself and the target to be measured using an internally mounted sensor. By this, it becomes possible to easily measure retroreflective coefficients using a commercially available mobile terminal having an imaging unit. As long as a handheld instrument in which all of the required hardware has been incorporated is used, the terminal device 1 can be realized simply by installing the program that realizes the function of the control unit 14.

Figure 12:
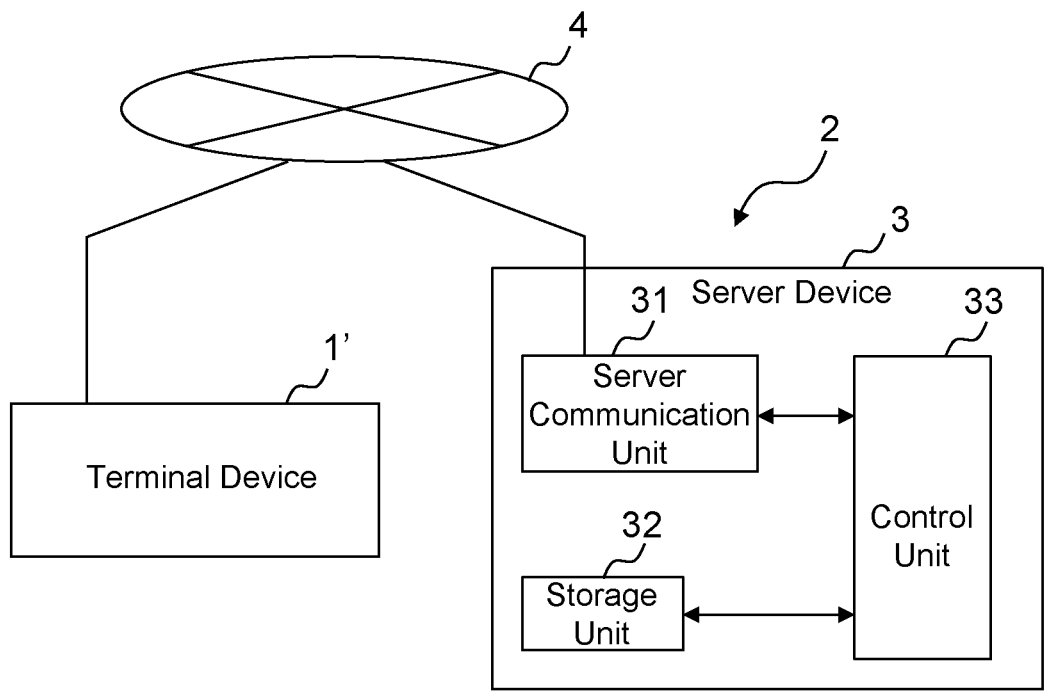
FIG. 12 is a schematic configuration diagram of a communication system 2.
Figure 13:
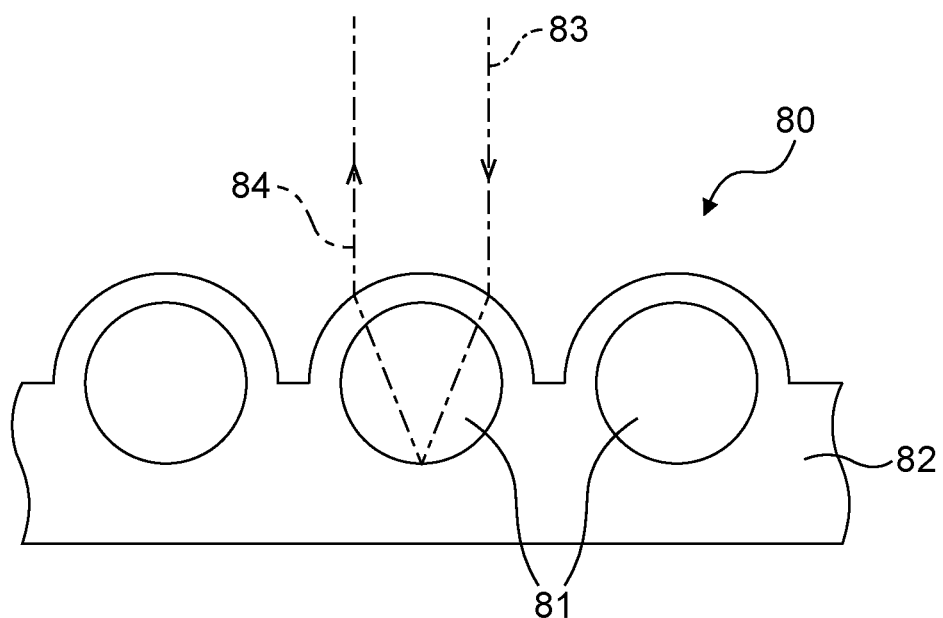
FIG. 13 is a drawing for describing a retroreflective material.

FIG. 12 is a schematic configuration diagram of a communication system 2. The communication system 2 includes a terminal device 1' and a server device 3 that are able to communicate one with the other. These devices are connected together through a wired or wireless communication network 4.

The terminal device 1' has the same configuration as the terminal device 1 described above. A difference from the terminal device 1 lies in the fact that the terminal device 1' sends image data of an image captured by the imaging unit 11 to the server device 3 without converting a luminance value or calculating a retroreflective coefficient from the image data, and receives the value of a retroreflective coefficient from the server device 3. A terminal communication unit of the terminal device 1' sends a first image captured by an imaging unit using light emitted for capture, a second image captured by the imaging unit without using the light emitted for capture, and the observation angle and entrance angle at the time of capture to the server device 3, and receives the value of a retroreflective coefficient from the server device 3. A display unit of the terminal device 1' displays the received value of the retroreflective coefficient, and the observation angle and entrance angle acquired within the terminal device 1', as well as the determination results therefor, in the same way as was done with the terminal device 1.

The server device 3 has a server communication unit 31, a storage unit 32 and a control unit 33. The server communication unit 31 receives a first image data, a second image data and the observation angle and entrance angle from the terminal device 1', and sends the value of the retroreflective coefficient to the terminal device 1'. The storage unit 32 stores the image data, capture information, and correspondence relationship data illustrated in FIG. 6A and FIG. 6B received from the terminal device 1', and all other data required to operate the server device 3. The control unit 33 is configured of a CPU, RAM, ROM, and the like, and has the same functionality as the control unit 14 of the terminal device 1. That is, the control unit 33 converts the capture information of the received image data to a luminance value of a target object, and then calculates the value of the retroreflective coefficient of the target object based on an illuminance value and the luminance value of the target object when the observation angle and the entrance angle are both included with a range of reference established in advance.

In this way, the display and capture of an image, the process for converting image data, and the process for calculating a required value may all be performed by different devices. If image processing is performed by a server device with high speed processing and large capacity, it becomes possible to realize faster and more accurate processing.

A computer program for realizing the functions of the control unit 14 of the terminal device 1 and the control unit 33 of the server device 3 on a computer may be provided in a form where the program is recorded to a recording medium that is readable using a computer such as a magnetic recording medium, an optical recording medium, and the like.

EXEMPLARY EMBODIMENTS

Item 1. A device comprising:
an imaging unit for capturing an image of a target object;
an observation angle acquiring unit for acquiring an observation angle determined by a positional relationship between the imaging unit, a light source for emitting light for capture and the target object;
an entrance angle acquiring unit for acquiring an entrance angle of light emitted for capture incident on the target object;
a converting unit for converting image data of an image to a luminance value of the target object using capture information of the image; and
a calculating unit for calculating a value of a retroreflective coefficient of the target object based on an illuminance value and the luminance value of the target object.

Item 2. The device according to Item 1 further comprising:
an output unit for outputting the values of the observation angle, the entrance angle, and the retroreflective coefficient.

Item 3. The device according to Item 2 further comprising:
a light emitting unit that is the light source for emitting light for capture.

Item 4. The device according to Item 2 or 3 further comprising:
a determining unit for determining whether the observation angle and entrance angle are included within a range of reference, wherein
the output unit also outputs determination results from the determining unit.

Item 5. The device according to Item 4 further comprising:
a storage unit for storing a correspondence relationship between the observation angle and the entrance angle that determines the range of reference.

Item 6. The device according to Item 5, wherein the storage unit stores a plurality of correspondence relationships based on the type of the target object, and the determining unit references correspondence relationships according to the type of the target object to be captured, and then determines whether the observation angle and the entrance angle are included within the obtained range of reference.

Item 7. The device according to Item 5 or 6, wherein the storage unit also stores a second correspondence relationship between the type of the light source, the observation angle, the entrance angle, and the illuminance value of the target object.

Item 8. The device according to any one of Items 4 to 7, wherein the imaging unit, in addition to capturing a first image of the target object using the light emitted for capture, also captures a second image of the target object without using the light emitted for capture, and the conversion unit, in addition to converting the image data of the first image to a first luminance value, also converts the image data of the second image to a second luminance value, and then acquires a luminance value of the target object by calculating the difference between the first luminance value and the second luminance value.

Item 9. The device according to any one of Items 4 to 8, wherein the imaging unit captures images that include portions other than the target object, and the conversion unit corrects the luminance value of the target object based on the portions other than the target object obtained from the image data of the image.

Item 10. The device according to any one of Items 4 to 9 further comprising:
an illuminance value calculating unit for calculating an illuminance value of the target object based on a luminance value of a retroreflective material when light is irradiated from the light source onto a retroreflective material for which the retroreflective coefficient is known.

Item 11. The device according to any one of Items 4 to 10, wherein the imaging unit, regardless of the operation of a user, captures an image of the target object when it has been determined that the observation angle and the entrance angle are included within the range of reference.

Item 12. The device according to any one of Items 4 to 11, wherein the output unit is a display unit for displaying an area captured by the imaging unit, the determination results of the determining unit, and the value of the retroreflective coefficient calculated by the calculating unit.

Item 13. The device according to any one of Items 1 to 12 further comprising:
an exposure correcting unit for adjusting an exposure amount during capture by the imaging unit.

Item 14. The device according to any one of Items 1 to 13 further comprising:
a filter for reducing the intensity of the light from the light source.

Item 15. The device according to any one of Items 1 to 14 further comprising:
a prism for deflecting the light path of the light from the light source, and then adjusting the observation angle.

Item 16. The device according to any one of Items 1 to 15 further comprising:
a reference target object that includes one or a plurality of retroreflective areas for which the retroreflective coefficients are known, wherein
the calculating unit performs calculation using the feature values of the one or the plurality of retroreflective areas.

Item 17. The device according to Item 16, wherein the reference target object includes a plurality of retroreflective areas for which the values of the retroreflective coefficients are known, and the retroreflective coefficients of the plurality of retroreflective areas are all different from one another.

Item 18. The device according to Item 17, wherein the plurality of retroreflective areas are arranged on the reference target object in a pattern determined in advance.

Item 19. A system that is a system including a terminal device and a server device that are capable of communicating one with another, wherein the terminal device has:
an imaging unit for capturing an image of a target object,
an observation angle acquiring unit for acquiring an observation angle determined by a positional relationship between the imaging unit, a light source for emitting light for capture, and the target object;
an entrance angle acquiring unit for acquiring an entrance angle of light emitted for capture incident on the target object;
a terminal communication unit for sending image data of an image to the server device and receiving a value of a retroreflective coefficient for the target object from the server device; and
a display unit for displaying the values of the observation angle, the entrance angle, and the retroreflective coefficient,
and wherein the server device has:
a conversion unit for converting image data to a luminance value of the target object using capture information of the image data;
a calculating unit for calculating a retroreflective coefficient for the target object based on an illuminance value and the luminance value of the target object; and
a server communication unit for receiving image data from the terminal device and sending the value of the retroreflective coefficient to the terminal device.

Item 20. A method comprising that steps of:
acquiring an observation angle determined by a positional relationship between an imaging unit for capturing an image of a target object, a light source for emitting light for capture, and the target object;
acquiring an entrance angle of light emitted for capture incident on the target subject;
irradiating light from the light source onto the target object;
capturing an image of the target object;
converting image data of an image to a luminance value of the target object using capture information of the image; and
calculating a value of a retroreflective coefficient for the target object based on an illuminance value and the luminance value of the target subject.

Item 21. A program in a computer that:
acquires an observation angle determined by a positional relationship between an imaging unit for capturing an image of a target object, a light source for emitting light for capture, and the target object;
acquires an entrance angle of light emitted for capture incident on the target subject;
converts image data of an image to a luminance value of the target object using capture information of an image of the target object captured by the imaging unit; and
calculates a value of a retroreflective coefficient for the target object based on an illuminance value and the luminance value of the target subject.

What is claimed is:
1. A device comprising:
an imaging unit for capturing an image of a target object;
an observation angle acquiring unit for acquiring an observation angle determined by a positional relationship between the imaging unit, a light source for emitting light for capture and the target object;
an entrance angle acquiring unit for acquiring an entrance angle of light emitted for capture incident on the target object;
a converting unit for converting image data of an image to a luminance value of the target object using capture information of the image; and a calculating unit for calculating a value of a retroreflective coefficient of the target object based on an illuminance value and the luminance value of the target object.

2. The device according to claim 1 further comprising:
an output unit for outputting the values of the observation angle, the entrance angle, and the retroreflective coefficient,
a determining unit for determining whether the observation angle and entrance angle are included within a range of reference, wherein
the output unit also outputs determination results from the determining unit.

3. The device according to claim 2 further comprising:
a storage unit for storing a correspondence relationship between the observation angle and the entrance angle that determines the range of reference.

4. The device according to claim 3, wherein the storage unit stores a plurality of correspondence relationships based on the type of the target object, and the determining unit references correspondence relationships according to the type of the target object to be captured, and then determines whether the observation angle and the entrance angle are included within the obtained range of reference.

5. The device according to claim 3, wherein the storage unit also stores a second correspondence relationship between the type of the light source, the observation angle, the entrance angle, and the illuminance value of the target object.

6. The device according to claim 2, wherein the imaging unit, in addition to capturing a first image of the target object using the light emitted for capture, also captures a second image of the target object without using the light emitted for capture, and the conversion unit, in addition to converting the image data of the first image to a first luminance value, also converts the image data of the second image to a second luminance value, and then acquires a luminance value of the target object by calculating the difference between the first luminance value and the second luminance value.

7. The device according to claim 2, wherein the imaging unit captures images that include portions other than the target object, and the conversion unit corrects the luminance value of the target object based on the portions other than the target object obtained from the image data of the image.

8. The device according to claim 2 further comprising:
an illuminance value calculating unit for calculating an illuminance value of the target object based on a luminance value of a retroreflective material when light is irradiated from the light source onto a retroreflective material for which the retroreflective coefficient is known.

9. The device according to claim 2, wherein the imaging unit, regardless of the operation of a user, captures an image of the target object when it has been determined that the observation angle and the entrance angle are included within the range of reference.

10. The device according to claim 2, wherein the output unit is a display unit for displaying an area captured by the imaging unit, the determination results of the determining unit, and the value of the retroreflective coefficient calculated by the calculating unit.

11. The device according to claim 1 further comprising:
an exposure correcting unit for adjusting an exposure amount during capture by the imaging unit.

12. The device according to claim 1 further comprising:
a filter for reducing the intensity of the light from the light source.

13. The device according to claim 1 further comprising:
a prism for deflecting the light path of the light from the light source, and then adjusting the observation angle.

14. The device according to claim 1 further comprising:
a reference target object that includes one or a plurality of retroreflective areas for which the retroreflective coefficients are known, wherein
the calculating unit performs calculation using the feature values of the one or the plurality of retroreflective areas.

15. The device according to claim 14, wherein the reference target object includes a plurality of retroreflective areas for which the values of the retroreflective coefficients are known, and the retroreflective coefficients of the plurality of retroreflective areas are all different from one another.

16. The device according to claim 15, wherein the plurality of retroreflective areas are arranged on the reference target object in a pattern determined in advance.

* * * * *